United States Patent
Rizo et al.

(10) Patent No.: US 12,171,778 B2
(45) Date of Patent: Dec. 24, 2024

(54) METHODS OF TREATING MYELODYSPLASTIC SYNDROME

(71) Applicant: Geron Corporation, Foster City, CA (US)

(72) Inventors: Aleksandra Rizo, Mount Kisco, NY (US); Jacqueline Cirillo Bussolari, Skillman, NJ (US)

(73) Assignee: Geron Corporation, Foster City, CA (US)

( * ) Notice: Subject to any disclaimer, the term of this patent is extended or adjusted under 35 U.S.C. 154(b) by 324 days.

(21) Appl. No.: 16/047,502

(22) Filed: Jul. 27, 2018

(65) Prior Publication Data

US 2019/0030064 A1 Jan. 31, 2019

Related U.S. Application Data

(60) Provisional application No. 62/685,542, filed on Jun. 15, 2018, provisional application No. 62/595,329, filed on Dec. 6, 2017, provisional application No. 62/538,315, filed on Jul. 28, 2017.

(51) Int. Cl.
| | | |
|---|---|---|
| *A61K 31/7125* | (2006.01) | |
| *A61K 9/00* | (2006.01) | |
| *A61K 47/54* | (2017.01) | |
| *A61P 7/00* | (2006.01) | |
| *C12N 15/113* | (2010.01) | |

(52) U.S. Cl.
CPC ........ *A61K 31/7125* (2013.01); *A61K 9/0019* (2013.01); *A61K 47/543* (2017.08); *A61P 7/00* (2018.01); *C12N 15/1137* (2013.01)

(58) Field of Classification Search
CPC .............. A61K 31/7125; A61K 9/0019; A61K 49/0423; A61P 7/00; B82Y 5/00; C12N 15/1135
See application file for complete search history.

(56) References Cited

U.S. PATENT DOCUMENTS

| | | |
|---|---|---|
| 5,583,016 A | 12/1996 | Villeponteau et al. |
| 5,656,638 A | 8/1997 | Gaeta et al. |
| 5,695,932 A | 12/1997 | West et al. |
| 5,760,062 A | 6/1998 | Gaeta et al. |
| 5,767,278 A | 6/1998 | Gaeta et al. |
| 5,770,613 A | 6/1998 | Gaeta et al. |
| 5,840,490 A | 11/1998 | Bacchetti et al. |
| 5,863,936 A | 1/1999 | Gaeta et al. |
| 5,952,490 A | 9/1999 | Hanecak et al. |
| 5,958,680 A | 9/1999 | Villeponteau et al. |
| 6,261,836 B1 | 6/2001 | Cech et al. |
| 6,331,399 B1 | 12/2001 | Monia et al. |
| 6,368,789 B1 | 4/2002 | West et al. |
| 6,444,650 B1 | 9/2002 | Cech et al. |
| 6,548,298 B2 | 4/2003 | Villeponteau et al. |
| 6,608,036 B1 | 8/2003 | Gryaznov et al. |
| 7,067,497 B2 | 6/2006 | Hanecak et al. |
| 7,321,029 B2 | 1/2008 | Gryaznov et al. |
| 7,485,717 B2 | 2/2009 | Gryaznov et al. |
| 7,494,982 B2 | 2/2009 | Gryaznov et al. |
| 7,563,618 B2 | 7/2009 | Gryaznov et al. |
| 7,989,428 B2 | 8/2011 | Go et al. |
| 7,989,603 B2 | 8/2011 | Gryaznov et al. |
| 7,998,938 B2 | 8/2011 | Moore et al. |
| 8,153,604 B2 | 4/2012 | Deen et al. |
| 8,377,644 B2 | 2/2013 | Gryaznov et al. |
| 8,440,635 B2 | 5/2013 | Gryaznov et al. |
| 8,906,615 B2 | 12/2014 | Gryaznov et al. |
| 9,133,233 B2 | 9/2015 | Gryaznov et al. |
| 9,375,485 B2 | 6/2016 | Stuart et al. |
| 9,388,415 B2 | 7/2016 | Gryaznov |
| 9,404,112 B2 | 8/2016 | Gryaznov |
| 11,123,359 B2 | 9/2021 | Tefferi |
| 2005/0113325 A1 | 5/2005 | Gryaznov et al. |
| 2005/0282893 A1 | 12/2005 | Au et al. |
| 2006/0009636 A1 | 1/2006 | Gryaznov et al. |
| 2006/0166221 A1 | 7/2006 | Bahou et al. |
| 2007/0015723 A1 | 1/2007 | Hanecak et al. |
| 2007/0224598 A1 | 9/2007 | Chang |
| 2007/0270363 A1 | 11/2007 | Bennett et al. |
| 2009/0162849 A1 | 6/2009 | Vainchenker et al. |

(Continued)

FOREIGN PATENT DOCUMENTS

| | | |
|---|---|---|
| CN | 101220044 | 7/2008 |
| JP | 2016-537423 | 12/2016 |

(Continued)

OTHER PUBLICATIONS

Tefferi et al (Blood Cancer Journal (2016) 6, e405; doi:10.1038/bcj.2016.13, 2 pages) (Year: 2016).*
Patnaik et al (Am. J. Hematol. 90(6): 550-559, 2015) (Year: 2015).*
Haase et al (Blood 110(13):4385-4395, 2007) (Year: 2007).*
UNC School of Medicine, History-Taking and Physical Examination | Medicine Clerkship (May 29, 2010), 3 pages, retrieved from https://www.med.unc.edu/medclerk/resources/cdim-sgim-guide/history-taking-and-physical-examinations/ (Year: 2010).*
Janssen Research & Development, LLC (ClinicalTrials.gov, https://clinicaltrials.gov/ct2/show/NCT02598661, Dec. 21, 2016) (Year: 2016).*
Smith (Am J Manag Care. 2010; 16:S59-S66) (Year: 2010).*

(Continued)

*Primary Examiner* — Richard A Schnizer
(74) *Attorney, Agent, or Firm* — Rudy J. Ng; Bozicevic, Field & Francis LLP

(57) ABSTRACT

This disclosure provides methods of treating a myelodysplastic syndrome (MDS) in a subject that is naive to treatment with an agent selected from a hypomethylating agent (HMA) and lenalidomide, or both. The method includes administering to the subject an effective amount of a telomerase inhibitor, such as e.g. imetelstat or imetelstat sodium. In some cases, the subject treated is classified as low or intermediate-1 IPSS risk MDS and/or have MDS relapsed/refractory to Erythropoiesis-Stimulating Agent (ESA).

39 Claims, 8 Drawing Sheets

Specification includes a Sequence Listing.

(56) References Cited

U.S. PATENT DOCUMENTS

| | | |
|---|---|---|
| 2009/0227681 A1 | 9/2009 | Dimock |
| 2010/0104586 A1 | 4/2010 | Tressler et al. |
| 2011/0263685 A1 | 10/2011 | Harley et al. |
| 2012/0322072 A1 | 12/2012 | Nygren |
| 2013/0253042 A1 | 9/2013 | Gryaznov et al. |
| 2014/0155465 A1 | 6/2014 | Bassett et al. |
| 2014/0163090 A1 | 6/2014 | Stuart et al. |
| 2014/0193518 A1 | 7/2014 | Sayeski et al. |
| 2014/0329890 A1 | 11/2014 | Gryaznov et al. |
| 2015/0005250 A1 | 1/2015 | Rollinson |
| 2015/0017119 A1 | 1/2015 | Fantl et al. |
| 2015/0299232 A1 | 10/2015 | Gryaznov et al. |
| 2015/0342982 A1 | 12/2015 | Stuart et al. |
| 2016/0287625 A1 | 10/2016 | Tefferi |
| 2017/0051287 A1 | 2/2017 | Stuart et al. |
| 2018/0036336 A1 | 2/2018 | Huang et al. |

FOREIGN PATENT DOCUMENTS

| | | |
|---|---|---|
| WO | 2001/018015 | 3/2001 |
| WO | 2002/077184 | 10/2002 |
| WO | 2004/029277 | 4/2004 |
| WO | 2005/023994 | 3/2005 |
| WO | 2006/113426 | 10/2006 |
| WO | 2007/016354 | 2/2007 |
| WO | 2008/054711 | 5/2008 |
| WO | 2008/112129 | 9/2008 |
| WO | 2010/045245 | 4/2010 |
| WO | 2011/017096 | 2/2011 |
| WO | 2011/098901 | 8/2011 |
| WO | 2013/059738 | 4/2013 |
| WO | 2014/085632 | 6/2014 |
| WO | WO 2014/088785 | 6/2014 |
| WO | 2014/160071 | 10/2014 |
| WO | 2015/069758 | 5/2015 |
| WO | 2018/026646 | 2/2018 |
| WO | WO 2019023667 | 1/2019 |

OTHER PUBLICATIONS

Adams, (1983) "Hindered dialkylamino nucleoside phosphite reagents in the synthesis of two DNA 51-mers," J. Am. Chem. Soc., 105:661-663.

Adema, V. and Bejar, R., (2013) "What lies beyond del(5q) in myelodysplastic syndrome?," Haematologica., 98(12): 1819-1821.

Ades, L. et al., (2014) "Myelodysplastic syndromes," Lancet, 383(9936):2239-2252.

Almeida, A., et al. (2017) "Recent advances in the treatment of lower-risk non-del(5q) myelodysplastic syndromes (MDS)", Leukemia Research, 52:50-57.

Asai et al., (2003) "A Novel Telomerase Template Antagonist (GRN163) as a Potential Anticancer Agent," Cancer Research, 63:3931-3639.

Baerlocher, G et al., (2013) "Imetelstat: A Novel Approach with Robust Hematologic and Molecular Responses in a Phase 2 study in Patients with Essential Thrombocythemia (ET) who are Refractory or Intolerant to Prior Therapy," Hematologica, 98(s1) Abstract S112.

Baerlocher, G., et al., (2012) "Imetelstat Rapidly Induces and Maintains Substantial Hematologic and Molecular Responses in Patients with Essential Thrombocythemia (ET) Who Are Refractory or Intolerant to Prior Therapy: Preliminary Phase II Results," Blood American Society of Hematology, 120(21):179.

Baerlocher, G., et al., (2015) "Telomerase inhibitor imetelstat in patients with essential thrombocythemia," N Engl J Med, 373:920-928.

Barbui et al., (2009) "Perspectives on thrombosis in essential thrombocythemia and polycythemia vera: is leukocytosis a causative factor?," Blood, 114:759-763.

Barosi et al., (2009) "Response criteria for essential thrombocythemia and polycythemia vera: result of a European LeukemiaNet consensus conference," Blood, 113(20):4829-4833.

Baxter et al., (2005) "Acquired mutation of the tyrosine kinase JAK2 in human myeloproliferative disorders," Lancet, 365:1054-1061.

Beaucage, (1981) "Deoxynucleoside phosphoramidites—A new class of key intermediates for deoxypolynucleotide synthesis," Tetra. Lett., 22:1859.

Beer et al., (2011) "How I treat essential thrombocythemia," Blood, 117(5):1472-1482.

Beier, F., et al., (2015) "Telomere dynamics in patients with del (5q) MDS before and under treatment with lenalidomide," Leukemia Research, 39(11): 1292-1298.

Belousov, (1997) "Sequence-specific targeting and covalent modification of human genomic DNA," Nucleic Acids Res., 5(25):3440-3444.

Blackburn, (1992) "Telomerases," Ann. Rev. Biochem., 61:113-129.

Blommers, (1994) "Effects of the Introduction of L-Nucleotides into DNA. Solution Structure of the Heterochiral Duplex d(G-C-G-(L)T-G-C-G).cntdot.d(C-G-C-A-C-G-C) Studied by NMR Spectroscopy" Biochemistry, 33:7886-7896.

Brassat, et al., (2011) "Functional p53 is required for effective execution of telomerase inhibition in BCR—ABL—positive CML cells," Experimental Hematology, 39(1):66-76.

Briatore, F., et al., (2009) "Increase of telomerase activity and hTERT expression in myelodysplastic syndromes," Cancer Biology & Therapy, 8(10): 883-889.

Brown, (1979) "Chemical synthesis and cloning of a tyrosine tRNA gene" Meth. Enzymol., 68:109.

Brunold, C. et al., (2011), "Imetelstat, A Potent Telomerase Inhibitor, Inhibits the Spontaneous Growth of CFU-Meg in Vitro From Essential Thrombocythemia Patients but Not From Healthy Individuals," Blood (ASH Annual Meeting Abstracts), 118: Abstract 3843.

Carobbio et al., (2007) "Leukocytosis is a risk factor for thrombosis in essential thrombocythemia: interaction with treatment, standard risk factors, and Jak2 mutation status" Blood, 109(6):2310-2313.

Carruthers, (1983) "Chemical Synthesis and Biological Studies on Mutated Gene-control Regions" Cold Springs Harbor Symp. Quant. Biol., 47:411-418.

Catenacci et al., (2005) "Myelodysplastic syndromes: A comprehensive Review," Blood Reviews, 19:301-319.

Cazzola and Invernizzi, (2011) "Ring sideroblasts and sideroblastic anemias," Haematologica, 96(6):789-792.

Chen et al., (2000) "Secondary Structure of Vertebrate Telomerase RNA" Cell, 100:503-514.

Crawford J, et al., (2009) "Relationship between changes in hemoglobin level and quality of life during chemotherapy in anemic cancer patients receiving epoetin alfa therapy," Cancer, 95(4): 888-895.

Della Porta M. G. & Malcovati L., (2011) "Myelodysplastic syndromes with bone marrow fibrosis," Haematologica, 96(2):180-183.

Drummond, M W. et al., (2005) "Dysregulated expression of the major telomerase components in leukemic stem cells," Leukemia, 19:381-389.

Ebrahim, A.S., et al., (2016) "Hematologic malignancies: new strategies to counter the BCL-2 protein," J. Cancer Res. Clin. Oncol., 142: 2013-2022.

El-Daly, H et al., (2005) "Selective Cytotoxicity and telomere damage in leukemia cells using the telomerase inhibitor BIBR1532," Blood, 105:1742-1749.

El-Kassar et al., (1997) "Clonality Analysis of Hematopoiesis in Essential Thrombocythemia: Advantages of Studying T Lymphocytes and Platelets" Blood, 89:128-134.

Fenaux, P, et al., (2011) "A randomized phase 3 study of lenalidomide versus placebo in RBC transfusion-dependent patients with Low-/Intermediate-1-risk myelodysplastic syndromes with del5q," Blood, 118(14):3765-3776.

Fenaux, P. and Ades, L., (2013) "How we treat lower-risk myelodysplastic syndromes," Blood, 121(21):4280-4286.

Fenaux, P., et al., (2017) "Efficacy and Safety of Imetelstat in RBC Transfusion-Dependent (TD) IPSS Low/Int-1 MDS Relapsed/Refractory to Erythropoiesis-Stimulating Agents (ESA) (IMerge)," Blood, 130: 4256.

(56) References Cited

OTHER PUBLICATIONS

Fialkow (1981) "Evidence that essential thrombocythemia is a clonal disorder with origin in a multipotent stem cell," Blood, 58:916-919.

Fili, C., et al., (2013) "Prospective phase II study on 5-days azacitidine for treatment of symptomatic and/or erythropoietin unresponsive patients with low/int-1-risk myelodysplastic syndromes" Clin Cancer Res., 19(12):3297-3308.

Fischer, U., et al. (2015) "Genomics and drug profiling of fatal TCF3-HLF-positive acute lymphoblastic leukemia identifies recurrent mutation patterns and therapeutic options," Nature Genetics, 47(9): 1020-1029.

Frenkel (1995) "7, 12-dimethylbenz[a]anthracene induces oxidative DNA modification in vivo," Free Radic. Biol. Med., 19:373-380.

Garcia-Manero, G., et al. (2011) "Hypomethylating agents and other novel strategies in myelodysplastic syndromes," J Clin Oncol., 29(5):516-523.

Graubert et al., (2012) "Recurrent mutations in the U2AF1 splicing factor in myelodysplastic syndromes," Nat Genet., 14(1):53-57.

Geron Corp., (2012) "Geron Corporation Reports Fourth Quarter and Annual 2012 Financial Results" Press Release.

Geron Corp., (2012), "Geron discontinues GRN1005 and Restructures to Focus on Imetelstat Development in Hematologic Malignancies and Solid Tumors with Short Telomeres," Press Release.

Geron Corp., (2013) "Geron Updates Imetelstat Development Strategy, Including Progress of Investigator-sponsored study in Myelofibrosis," Press Release.

Gianelli U. et al., (2012) "The European Consensus on grading of bone marrow fibrosis allows a better prognostication of patients with primary myelofibrosis," Modern Pathol., 25(9):1193-1202.

Gnatenko et al., (2003) "Transcript profiling of human platelets using microarray and serial analysis of gene expression," Blood, 101:2285-2293.

Greenberg, P., et al., (1997) "International scoring system for evaluating prognosis in myelodysplastic syndromes," Blood, 89(6):2079-2088.

Gryaznov and Letsinger, (1992) "Synthesis and properties of oligonucleotides containing aminodeoxythymidine units," Nucleic Acids Research, 20(13):3403-3409.

Gryaznov and Lloyd, (1993) "Modulation of oligonucleotide duplex and triplex stability via hydrophobic interactions," Nucleic Acids Research, 21(25):5909-5915.

Gryaznov and Winter, (1998) "RNA mimetics: oligoribonucleotide N3'-P5' phosphoramidates," Nucleic Acids Research, 26(18):4160-4167.

Gryaznov et al., (1996) "Oligonucleotide N3'-P5' phosphoramidates as antisense agents," Nucleic Acids Research, 24(8):1508-1514.

Gryaznov et al., (1999) "Oligonucleotide N3'-P5' phosphoramidates as potential therapeutic agents," Biochimica at Biophysica Acta, 1489, 131-140.

Gryaznov et al., (2001) "Telomerase Inhibitors—Oligonucleotide Phosphoramidates as Potential Therapeutic Agents," Nucleosides, Nucleotides & Nucleic Acids, 20(4-7):401-410.

Gryaznov et al., (2003) "Oligonucleotide N3'→P5' Thio-phosphoramidate Telomerase Template Antagonists as Potential Anticancer Agents," Nucleosides, Nucleotides & Nucleic Acids, 22(5-8):577-581.

Gryaznov et al., (2010) "Oligonucleotide N3'-P5' Phosphoramidates and Thio-Phosphoramidates as Potential Therapeutic Agents," Chemistry & Biodiversity, 7:477-493.

Gryaznov et al., (2012) "Oligonucleotide N3'-P5' Phosphoramidates and Thio-Phoshoramidates as Potential Therapeutic Agents," in Chemistry and Biology of Artificial Nucleic Acids, Egli and Herdewijn Eds., Wiley-VCH, 2012, pp. 61-77.

Hanahan et al., (1997) "Hallmarks of Cancer: The Next Generation," Cell, 144:646-674.

Harley (1991) "Telomere loss: mitotic clock or genetic time bomb?," Mutation Research, 256:271-282.

Harley, C. et al., (1997), "Telomerase, Checkpoints and Cancer," Cancer Surv., 29:263-284.

Hellstrom-Lindberg, E., et al., (2003) "A validated decision model for treating the anaemia of myelodysplastic syndromes with erythropoietin + granulocyte colony-stimulating factor: significant effects on quality of life," Br J Haematol., 120(6):1037-1046.

Hennessy B. T., et al., (2004) "New Approaches in the Treatment of Myelofibrosis," Cancer, 103(1):32-43.

Herbert B-S, et al., (2005) "Lipid modification of GRN163, an N3'-P5' thio-phosphoramidate oligonucleotide, enhances the potency of telomerase inhibition," Oncogene, 24:5262-5268.

Hochreiter, A. et al., (2006), "Telomerase template antagonist GRN163L disrupts telomere maintenance, tumor growth, and metastasis of breast cancer," Clin. Cancer Res. 12(10):3184-92.

James et al., (2005) "A unique clonal JAK2 mutation leading to constitutive signalling causes polycythaemia vera," Nature, 434:1144-1148.

Joseph, I. et al., (2010), "The Telomerase Inhibitor Imetelstat Depletes Cancer Stem Cells in Breast and Pancreatic Cancer Cell Lines," Cancer Research Online, 70:9494-9504.

Kelaidi, C. et al., (2013) "Long-term outcome of anemic lower-risk myelodysplastic syndromes without 5q deletion refractory to or relapsing after erythropoiesis-stimulating agents," Leukemia, 27(6):1283-1290.

Kelland, L. R., (2005) "Overcoming the immortality of tumour cells by telomere and telomerase based cancer therapeutics," Eur. J Cancer, 41:971-979.

Keller, G et al., (2009) "Telomeres and telomerase in chronic myeloid leukemia: impact for pathogenesis disease progression and targeted therapy," Hematological Oncology, 27(3):123-129.

Kim et al., (2001) "A low threshold level of expression of mutant-template telomerase RNA inhibits human tumor cell proliferation," Proc. Natl. Acad. Sci. USA, 98(14):7982-7987.

Kim, N. et al., (1994) "Specific association of human telomerase activity with immortal cells and cancer," Science, 266:2011-4.

Kralovics et al., (2005) "A Gain-of-Function Mutation of JAK2 in Myeloproliferative Disorders," N Engl. J Med., 352:1779-1790.

Kupihar et al., (2001) "Synthesis and Application of a Novel, Crystalline Phosphoramidite Monomer with Thiol Terminus, Suitable for the Synthes," Bioorg. Med. Chem., 9:1241-1247.

Lange, K., et al., (2010) "Telomere shortening and chromosomal instability in myelodysplastic syndromes", Genes Chromosomes & Cancer., 49(3):260-269.

Lasho et al., (2012) "SRSF2 mutations in primary myelofibrosis: significant clustering with IDH mutations and Independent association with inferior overall and leukemia-free survival," Blood, 120(20):4168-4171.

Lebedeva et al., (2001) "Antisense Oligonucleotides: Promise and Reality," Annual Review of Pharmacology and Toxicology, 41:403-419.

Lee, J.-J. et al., (2003) "Telomere length shortening in non-Hodgkin's lymphoma patients undergoing chemotherapy," Ann. Hematol. 82:492-5.

Levine et al., (2005) "Activating mutation in the tyrosine kinase JAK2 in polycythemia vera, essential thrombocythemia, and myeloid metaplasia with myelofibrosis" Cancer Cell, 7:387-397.

Loiseau, C. et al., (2015) "New therapeutic approaches in myelodysplastic syndromes: hypomethylating agents and lenalidomide," Exp Hematol., 43(8):661-72.

Ly, H. et al., (2005) "Functional characterization of telomerase RNA variants found in patients with hematologic disorders," Blood, 105(6):2332-2339.

Macejak et al., (1999) "Adenovirus-Mediated Expression of a Ribozyme to c-myb mRNA Inhibits Smooth Muscle Cell Proliferation and Neointima Formation in Vivo," Journal of Virology, 73 (9):7745-7751.

Makishima et al., (2012) "Mutations in the spliceosome machinery, a novel and ubiquitous pathway in leukemogenesis," Blood, 119(14):3203-3210.

Malcovati, L. et al., (2005) "Prognostic factors and life expectancy in myelodysplastic syndromes classified according to WHO criteria: a basis for clinical decision making," J Clin Oncol, 23:7594-7603.

Malcovati, L. et al., (2006) "Predicting survival and leukemic evolution in patients with myelodysplastic syndrome," Haematologica, 91:1588-1590.

(56) References Cited

OTHER PUBLICATIONS

Maritz, M F. et al., (2010) "Targeting telomerase in Hematologic malignancy," Future Oncology, 6(5):769-789.
McCurdy et al., (1997) "An Improved Method for the Synthesis of N3'→P5' Phosphoramidate Oligonucleotides," Tetrahedron Letters, 38:207-210.
Meggendorfer et al., (2012) "SRSF2 mutations in 275 cases with chronic myelomonocytic leukemia (CMML)," Blood, 120(15):3080-3088.
Mergny J.-L, et al., (2002) "Natural and pharmacological regulation of telomerase," Nucleic Acids Res., 30(4):839-365.
Mishra et al., (1995) "Improved leishmanicidal effect of phosphorotioate antisense oligonucleotides by LDL-mediated delivery," Biochim. Et Biophys. Acta, 1264:229-237.
Narang (1979) "[6] Improved phosphotriester method for the synthesis of gene fragments," Meth. Enzymol., 68:90.
Nelson et al., (1997) "N3'->P5' Oligodeoxyribonucleotide Phosphoramidates: A New Method of Synthesis Based on a Phosphoramidite Amine-Exchange Reaction," J Org. Chem., 62:7278-7287.
Nimer (1999) "Essential Thrombocythemia: Another "Heterogeneous Disease" Better Understood?," Blood, 93:415-416.
Oliva, EN, et al., (2013) "Biological activity of lenalidomide in myelodysplastic syndromes with del5q: results of gene expression profiling from a multicenter phase II study", Ann Hematol., 92(1):25-32.
Papaemmanuil et al., (2011) "Somatic SF3B1 Mutation in Myelodysplasia with Ring Sideroblasts," N Engl J Med. 365(15):1384-1395.
Park, S, et al., (2017) "Outcome of lower-risk patients with myelodysplastic syndromes without 5q deletion after failure of erythropoiesis-stimulating agents," dJ Clin Oncol., 35(14):1591-1597.
Pascolo et al., (2002) "Mechanism of Human Telomerase Inhibition by BIBR1532, a Synthetic, Non-nucleosidic Drug Candidate," J. Biol. Chem., 277(18):15566-15572.
Pongracz and Gryaznov (1999) "Oligonucleotide N3'→P5' thiophosphoramidates: synthesis and properties," Tetrahedron Letters, 49:7661-7664.
Pongracz et al., (2003) "Novel Short Oligonucleotide Conjugates as Inhibitors of Human Telomerase," Nucleosides, Nucleotides & Nucleic Acids, 22(5-8):1627-1629.
Pruzan, R. et al., (2002) "Allosteric inhibitors of telomerase: oligonucleotide N3'→P5' phosphoramidates," Nucl. Acids Res., 30(2):559-68.
Puri et al., (2012) "Novel Therapeutics Targeting Telomerase and Telomeres," J. Cancer Sci. Ther., 5:e127.
Ratain, M. et al., (2008) "A phase I trial of GRN163L (GRN), a first-in-class telomere inhibitor, in advanced solid tumors," J. Clin. Oncol. 26:3581.
Romero, D., (2015) "Haematological Cancer-Promising Results of BCL2 Inhibition," Nature Reviews Clinical Oncology, 12(9):504.
Ropio, J., et al., (2016), "Telomerase Activation in Hematological Malignancies," Genes, 7(9):E61.
Roth, A et al., (2003) "Telomerase is limiting the growth of acute myeloid leukemia cells," Leukemia, 17(12):2410-2417.
Roth, A et al., (2007) "Short Telomeres and High Telomerase Activity in T-cell Prolymphocytic Leukemia," Leukemia 21:2456-2462.
Roth, A et al., (2010) "Imetelstat (GRN163L)-telomerase-based cancer therapy," Recent Results in Cancer Research, 184:221-234.
Ruden, M. et al., (2013) "Novel anticancer therapeutics targeting telomerase," Cancer Treatment Reviews, 39: 444-456.
Ruella, M. et al., (2010) "Telomere length in pH-negative chronic myeloproliferative neoplasms: it is reduced according to JAK2 V617F mutation allele burden and it is not affected by cytoreductive treatment with hydroxyurea," ASH Annual Meeting Abstracts 116:1975.
Rump et al., (1995) "Preparation of Conjugates of Oligodeoxynucleotides and Lipid Structures and Their Interaction with Low-Density Lipoprotein," Bioconj. Chem., 9:341-349.

Shaffer, Catherine (2012), "Geron Hit Hard by Termination of Phase II Brain Cancer Trial," Bioworld Today, 23(235), 1, 4, 7.
Shammas, M.A., et al. (2008), "Telomerase inhibitor GRN163L inhibits myeloma cell growth in vitro and in vivo," Leukemia, 22(7):1410-8.
Shay, J. et al., (1997), "A survey of telomerase activity in human cancer," Eur. J. Cancer, 33:787-91.
Shea, R. et al., (1990) "Synthesis, hybridization properties and antiviral activity of lipid-oligodeoxynucleotide conjugates," Nucl. Acids Res., 18(13): 3777-83.
Shea-Herbert, B. et al., (1999) "Inhibition of human telomerase in immortal human cells leads to progressive telomere shortening and cell death," Proc. Natl. Acad. Sci. USA, 96(25):14276-81.
Shea-Herbert, B. et al., (2002) "Oligonucleotide N3'→P5' phosphoramidates as efficient telomerase inhibitors," Oncogene, 21:638-42.
Shea-Herbert, B. et al., (2005) "Lipid modification of GRN163, an N3'-P5' thio-phosphoramidate oligonucleotide, enhance the potency of telomerase inhibition," Oncogene, 24:5262-8.
Silver R. T., (2004) "Myelofibrosis: Thalidomide Finds a New Disease," Mayo Clin. Proc., 79(7):857-858.
Sole, F. et al. (2005), "Identification of novel cytogenetic markers with prognostic significance in a series of 968 patients with primary myelodysplastic syndromes," Haematologica, 90(9):1168-78.
Steensma, DP, et al., (2015) "Myelodysplastic syndromes: diagnosis and treatment," Mayo Clinic Proc., 90(7):969-983.
Sumi, M et al., (2004) "A G-quadruplex interactive agent, telomestatin (SOT-095) induces telomere shortening with apoptosis and enhances chemosensitivity in acute myeloid leukemia," International Journal of Oncology, 24(6):1481-1487.
Tauchi et al., (2003) "Activity of a Novel G-Quadruplex-Interactive Telomerase Inhibitor, SOT-095, Against Human leukemia Cells: Involvement of ATM-Dependent DNA Damage Response Pathways," Blood, American Society of Hematology, 102(11):652a.
Tefferi A., et al., (2015) "A pilot study of the telomerase inhibitor imetelstat for myelofibrosis," N Engl J Med., 373:908-919.
Theophile, K. et al (2008) "The expression levels of telomerase catalytic subunit hTERT and oncogenic MYC in essential thrombocythemia are affected by the molecular subtype," Ann Hematol., 87(4):263-8.
Thepot, S., et al., (2016) "A randomized phase II trial of azacitidine +/− epoetin-? in lower-risk myelodysplastic syndromes resistant to erythropoietic stimulating agents," Haematologica, 101(8):918-925.
Thol et al., (2011) "Prognostic significance of ASXL1 mutations in patients with myelodysplastic syndromes," J Clin Oncol., 29(18):2499-506.
Thompson, P. A. et al., (2013), "A Phase I Trial of Imetelstat in Children with Refractory or Recurrent Solid Tumors: A Children's Oncology Group Phase l Consortium Study (ADVL 1112)," Clinical Cancer Research, 1-7.
Tobiasson, M, et al., (2014) "Limited clinical efficacy of azacitidine in transfusion-dependent, growth factor-resistant, low-and Int-1-risk MDS: Results from the nordic NMDSG08A phase II trial," Blood Cancer J., 4, e189; doi:10.1038/bcj.2014.8.
Uhlmann and Peyman (1990) "Antisense oligonucleotides: a new therapeutic principle," Chemical Reviews, 90:543-584.
US National Institutes of Health, "Imetelstat Sodium in Treating Patients with Primary or Secondary Myelofibrosis," clinicaltrials. gov NCT01731951, 2012.
US National Institutes of Health, "Open Label Study to Evaluate the Activity of Imetelstat in Patients with Essential Thrombocythemia or Polycythemia (ET/PV)," clinicaltrials.gov NCT01243073, 2010.
Van Ziffle, et al., (2003) "Telomere length in subpopulations of human hematopoetic cells," Stem Cells, 21:654-660.
Vardiman, JW, et al. (2009) "The 2008 revision of the World Health Organization (WHO) classification of myeloid neoplasms and acute leukemia: rationale and important changes," Blood, 114(5):937-951.
Wang, et al., (2004) "Telomerase inhibition with an oligonucleotide telomerase template antagonist: in vitro and in vivo studies in multiple myeloma and lymphoma", Blood, 103(1):258-266.

(56) References Cited

OTHER PUBLICATIONS

Ward and Autexier (2005) "Pharmacological Telomerase Inhibition Can Sensitize Drug-Resistant and Drug-Sensitive Cells to Chemotherapeutic Treatment," Mol. Pharmacol., 68:779-786.
Wu, K.-J et al., (1999) "Direct activation of TERT transcription by c-MYC," Nature Genetics 21:220-224.
Yoon, S. Y. et al., (2007), "Telomere length shortening of peripheral blood mononuclear cells in solid-cancer patients undergoing standard-dose chemotherapy might be correlated with good treatment response and neutropenia severity," Acta Haematol., 118: 30-7.
Zeng et al., (2003) "MicroRNAs and small interfering RNAs can inhibit mRNA expression by similar mechanisms," Proc. Natl. Acad. Sci. USA, 100(17):9779-9784.
Ziakas (2008) "Effect of JAK2 V617F on Thrombotic Risk in Patients With Essential Thrombocythemia: Measuring The Uncertain," Haematologica, 93:1412-1414.
European Search Report issued in EP 16197293.0 dated Apr. 12, 2017.
Supplementary European Search Report issued in EP 13861008.4 dated Aug. 22, 2016.
International Search Report issued in PCT/US2013/070437 mailed Jan. 22, 2014.
International Search Report and Written Opinion issued in PCT/US2018/044225 mailed Oct. 10, 2018.
Tefferi et al., (2016) "Imetelstat therapy in, refractory anemia with ring sideroblasts with or without thrombocytosis", Blood Cancer Journal, 6(3): e405.
Shammas, MA, et al., 2008 "Telomerase inhibitor GRN163L inhibits myeloma cell growth in vitro and in vivo", Leukemia, 22(7):1410-1418.
Haase, Detlef, et al., (2007) "New insights into the prognostic impact of the karyotype in MDS and correlation with subtypes: evidence from a core dataset of 2124 patients", Blood, 110(13):4385-4395.
Patnaik, Mrinal and Tefferi, Ayalew, (2015) "CME Information: Refractory anemia with ring sideroblasts and RARS with thrombocytosis", American Journal of Hematology, 90(6):549-559.
European Search Report for EP 13861008.4 dated Aug. 22, 2016.
European Search Report issued in European Application No. EP16197293.0 dated Apr. 5, 2017.
Geron Corporation, U.S. Appl. No. 16/432,727, filed Jun. 5, 2019, now abandoned.
Geron Presents Positive Results from Phase 2 Study of Imetelstat in Essential Thrombocythemia at the American Society of Hematology Annual Meeting, Press Release [online], Geron Corporation (retrieved on Jul. 17, 2019), Dec. 10, 2012.
International Search Report for PCT/US2013/070437 dated Jan. 22, 2014.
International Search Report issued in PCT/US2017/044348 mailed Oct. 10, 2017.
International Search Report issued in PCT/US2018/044225 mailed Oct. 10, 2018.
Kakiuchi et al. (2010) "Inhibition of Human Tumor Cell Proliferation by the Telomerase Inhibitor TELIN" Cytologia 75:2 177-183.
Kim et al., (2010) "Telomerase Activity Is High In Essential Thrombocythemia and Polycythemia Vera, but Not In Myelofibrosis—a Comprehensive Analysis on Telomerase Activity and Cytogenetics In Myeloproliferative Neoplasm and Myelodysplastic Syndromes" Blood 116:21 4462.
Pallis et al., (2009) "The Telomerase Inhibitor RHPS4 Induces Telomere Shortening, DNA-Damage and Cell Death in AML Cells and Chemosensitises Cells to Daunorubicin" Blood 114:22 2760.
Spanoudakis et al., (2011) "Dynamics of Telomere's Length and Telomerawe Activity in Philadelphia Chromosom Negative Myeloproliferative Neoplasms" Leukemia Research 35:4 459-464.
Tokcaer-Keskin et al., (2010) "The Effect of Telomerase Template Antagonist GRN163L on Bone-marrow-derived Rat Mesenchymal Stem Cells is Reversible and Associated with Altered Expression" Stem Cell Rev Rep. 6:2 224-233.

Wu et al., (2010) "GRN163L, a Telomerase Inhibitor for Cancer Treatment".
Paulsson, et al., (2007), Patholngic Biolog, 55:37-48.
Baerlocher, et al. (2019) "Imetelstat Inhibits Growth of Megakaryocyte Colony-forming Units From Patients with Essential Thrombocythemia" Blood Advances, vol. 3, No. 22, pp. 3724-3728.
Bieche, et al. (2000) "Quantitation of hTERT Gene Expression in Sporadic Breast Tumors with a Real-Time Reverse Transcription-Polymerase Chain Reaction Assay" Clin Cancer Res, vol. 6, pp. 452-459.
Blasco, et al. (1997) "Telomere Shortening and Tumor Formation by Mouse Cells Lacking Telomerase RNA" Cell, vol. 91, pp. 25-34.
Bruedigam, et al. (2014) "Telomerase Inhibition Effectively Targets Mouse and Human AML Stem Cells and Delays Relapse Following Chemotherapy" Cell Stem Cell, 15, pp. 775-790.
Cervantes (2014) "How I treat myelofibrosis", Blood, vol. 124(17), pp. 2635-2642.
Briatore, et al. (2009) "Increase of telomerase activity and hTERT expression in myelodysplastic syndromes" Cancer Biology and Therapy, 8(10) pp. 883-889.
Gissingler, et al. (2016) "Impact of High Molecular Risk Mutations on Overall Survival in WHO-Defined Essential Thrombocythemia and Prefibrotic Primary Myelofibrosis" Blood, vol. 128, p. 193.
Greenberg, et al. (2012) "Revised International Prognostic Scoring System for Myelodysplastic Syndromes" Blood, vol. 120, No. 12, pp. 2454-2465.
Guglielmelli, et al. (2014) "The number of prognostically detriment mutations and prognosis in primary myelofibrosis: an international study of 797 patients" Leukemia, vol. 28, No. 9, pp. 1804-18010.
Harley, C., et al. (1990) "Telomeres shorten during ageing of human fibroblasts" Nature 345, pages pp. 458-60.
Hu, et al. (2019) "Combination Treatment with Imetelstat, a Telomerase Inhibitor, and Ruxolitinib Depletes Myelofibrosis Hematopoietic Stem Cells and Progenitor Cells" Blood, 13, vol. 134, Suppl. 1, p. 1.
Hultdin, M, et al. (1998) "Telomere analysis by fluorescence in situ hybridization and flow cytometry" Nucl. Acids Res. 26(16), pp. 3651-3656.
Janssen Research & Development L (2017) "Study to Evaluate Imetelstat (JNJ-63935937) in Subjects With International Prognostic Scoring System (IPSS) Low or Intermediate-1 Risk Myelodysplastic Syndrome (MDS)" ClinicalTrials.gov Jun. 29, 2017 https://clinicaltrials.gov/ct2/history/NCT02598661?V_20=View#StudyPageTop.
Jie, Jin, et al. (2005) "Down Regulation of hTERT is an Important Mechanism in Apoptosis of MUTZ-1 Cells Induced by As203" Blood, American Society of Hematology, vol. 106, No. 11, p. 4910.
Kuykendall, et al. (2018) "Between a rux and a hard place: evaluating salvage treatment and outcomes in myelofibrosis after ruxolitinib discontinuation" Annals of Hematology, vol. 97, pp. 435-441.
Langabeer, et al. (2016) "Chasing down the triple-negative myeloproliferative neoplasms: Implications for molecular diagnostics" JAK-STAT, vol. 5, pp. e1248011-1-e1248011-5.
Leibundgut, Elisabeth Oppliger., et al. (2015) "Dynamics of Mutations in Patients with ET Treated with Imetelstat" Blood, vol. 126, No. 23, p. 57.
Marty, et al. (2016) "Calreticulin mutants in mice induce an MPL-dependent thrombocytosis with frequent progression to myelofibrosis" Blood, vol. 127(10), pp. 1317-1324.
Mascarenhas, et al. (2018) "Imetelstat is effective treatement for patients with intermediate-2 or high-risk myelofibrosis who have relapsed on or are refractory to janus kinase inhibitor therapy: results of a phase 2 randomized study of two dose levels" Blood, 132(supplement 1), p. 685.
McNamara, C, et al. EHA; Amsterdam, the Netherlands; Jun. 13, 2019. #PS1460.
The Merck Manual, 18th Edition, 1159-1162.
Mesa, et al. (2016) "Individualizing Care for Patients with Myeloproliferative Neoplasms: Integrating Genetics, Evolving Therapies, and Patient-Specific Disease Burden" Am Soc Clin Oncol Educ Book, vol. 35, pp. 324-335.

(56) References Cited

OTHER PUBLICATIONS

Mosoyan, et al. (2017) "Imetelstat, a telomerase inhibitor, differentially affects normal and malignant megakaryopoiesis" Leukemia, vol. 31, pp. 2458-2467.

Mudireddy, et al. (2018) "Prefibrotic versus overtly fibrotic primary myelofibrosis: clinical, cytogenetic, molecular and prognostic comparisons" Bri J. Haematol., vol. 182, pp. 594-597.

Newberry, et al. (2017) "Clonal evolution and outcomes in myelofibrosis after ruxolitinib discontinuation" Blood, vol. 130, No. 9, pp. 1125-1131.

Palandri, F, et al. (2020) "Life After Ruxolitinib: Reasons for Discontinuation, Impact of Disease Phase, and Outcomes in 218 Patients with Myelofibrosis" Cancer 126(6), pp. 1243-1252.

Palma, et al. (2013) "Telomere length and Expression of Human Telomerase Reverse Transcriptase Splice Variants in Chronic Lymphocytic Leukemia" Experimental Hematology, vol. 41, pp. 615-626.

Pardanani, et al. (2014) "Definition and managment of ruxolitinib treatment failure in myelofibrosis" Blood Cancer Journal, vol. 4, p. e268.

Patel, et al. (2015) "Correlation of mutation profile and response in patients with myelofibrosis treated with ruxolitinib" Blood, vol. 126, No. 6, pp. 790-797.

Patnaik, M, et al. (2017) "Refractory anemia with ring sideroblasts (RARS) and RARS with thrombocytosis (RARS-T): 2017 update on diagnosis, risk-stratification, and management" American Journal of Hematology, vol. 92, No. 3, pp. 297-310.

Prebet et al., (2017) "Outcome of patients treated for myelodysplastic syndromes without deletion 5q after failure of lenalidomide therapy" Oncotarget, 8:23.

Rufer, N., et al. (1998) "Telomere length dynamics in human lymphocyte subpopulations measured by flow cytometry" Nature Biotechnology 16, pp. 743-7.

Rumi, et al. (2014) "Clinical effect of driver mutations of JAK2, CALR, or MPL in primary myelofibrosis" Blood, col. 124(7), pp. 1062-1069.

Schain, F, et al. (2019) "Survival outcomes in myelofibrosis patients treated with ruxolitinib: A population-based cohort study in Sweden and Norway" Eur J Haematol. 103, pp. 614-619.

Shammo, et al. (2016) "Mutations in MPNs: prognostic implications, window to biology, and impact on treatment decisions" Hematology Am Soc Hematol Educ Program, vol. 2016(1), pp. 552-560.

Shreenivas, et al. (2018) "Emerging drugs for the treatment of Myelofibrosis" Expert Opinion on Emerging Drugs, vol. 23, No. 1, pp. 37-49.

Sochacki, et al. (2016) "Therapeutic approaches in myelofibrosis and myelodysplastic/myelolproliferative overlap syndromes" Onco. Targets Ther. vol. 9, pp. 2273-2286.

Spiegel, et al. (2017) "Impact of genomic alterations on outcomes in myelofibrosis patients undergoing JAK1/2 inhibitor therapy" Blood Adv., vol. 1, No. 20, pp. 1729-1738.

Tefferi, A, et al. (2013) "Imetelstat, a Telomerase Inhibitor, Induces Morphologic and Molecular Remissions in Myelofibrosis and Reversal of Bone Marrow Fibrosis" Blood, retrieved from the internet: URL:http://www.bloodjournal.org/content/122/21/662 [retrieved on May 26, 2017].

Tefferi, A, et al. (2014) "Long-term survival and blast transformation in molecularly annotated essential thrombocythemia, polycythemia vera, and myelofibrosis" Blood, vol. 124, No. 16, pp. 2507-2513.

Tefferi, A, et al. (2016) "The telomerase inhibitor imetelstat in patients (pts) with intermediate-2 or high-risk myelofibrosis (MF) previously treated with Janus kinase (JAK) inhibitor: A phase 2, randomized study." Journal of Clinical Oncology, vol. 34, Supp 15 Abstract No. TPS7079.

Terrin, et al. (2007) "Telomerase expression in B-cell chronic lymphocytic leukemia predicts survival and delineates subgroups of patients with the same igVH mutation status and different outcome" Leukemia, vol. 21, pp. 965-972.

Vannucchi, et al. (2013) "Mutations and prognosis in primary myelofibrosis" Leukemia, vol. 27, pp. 1861-1869.

Vasko, et al. (2017) "Telomeres and Telomerase in Hematopoietic Dysfunction: Prognostic Implications and Pharmacological Interventions" Int J Mol Sci., vol. 18(11), pp. 1-14.

Wang, et al. (2014) "Atypical chronic myeloid leukemia is clinically distinct from unclassifiable myelodysplastic/myeloproliferative neoplasms" Blood, vol. 123, No. 17, pp. 2645-2651.

Wang, et al. (2018) "Imetelstat, a telomerase inhibitor, is capable of depleting myelofibrosis stem and progenitor cells" Blood Adv., vol. 2, No. 18, pp. 2378-2388.

Dong, et al. (2016) "MDS shows a higher expression of hTERT and alternative splice variants in unactivated T-cells" Oncotarget, vol. 7, No. 44, pp. 71904-71914.

Zijlmans, et al. (1997) "Telomeres in the mouse have large interchromosomal variations in the number of T2AG3 repeats" Proc. Natl. Acad. Sci. USA, vol. 94, pp. 7423-7428.

Clinical Trials, (2015) "Study to Evaluate Imetelstat (GRN163L) in Subjects With International Prognostic Scoring System (IPSS) Low or Intermediate-1 Risk Myelodysplastic Syndrome (MDS)", Geron Corporation, 20 pages, NCT ID: NCT02598661.

Kishtagari et al., (2017) "Biological and clinical implications of telomere dysfunction in myeloid malignancies", Ther Adv Hematol., 8(11):317-326.

Tefferi et al., (2015) "Telomerase Inhibitor Imetelstat Therapy in Refractory Anemia with Ring Sideroblasts with or without Thrombocytosis", Clinical Trial, 4 pages.

Almeida et al., "Recent advances in the treatment of lower-risk non-del(5q) myelodysplastic syndromes (MDS)", Leukemia Research, 52 (2017) 50-57.

Baerlocher et al. (2015) "Supplementary Appendix" New England Journal of Medicine, vol. 373, total 41 pages.

Drevon et al., "Myelodysplastic syndrome (MDS) with isolated trisomy 8: a type of MDS frequen. tly associated with myeloproliferative features? A report by the Groupe Francophone des Myelodysplasies". British Journal of Haematology, vol. 182, No. 6; pp. 843-850 (Published: 2018).

Rusbuldt et al., (2016) "Abstract 2731: Impact of hypomethylating agents on hTERT expression and synergistic effect in combination with imetelstat, a telomerase inhibitor, in AML cell lines" Cancer Research, American Association for Cancer Research, 1-2.

Santini; "Treatment of low-risk myelodysplastic syndromes", Hematology Am Soc Hematol Educ Program, 1; pp. 162-469 (Published 2016).

The Merck Manual, 18th Edition, 1099-1105. (Published 2006).

Anonymous, (2016) "Abstract 2731: Impact of hypomethylating agents on hTERT expression and synergistic effect in combination with imetelstat, a telomerase inhibitor, in AML cell lines | Cancer Research | American Association for Cancer Research", pp. 1-2.

Fragkiadaki et al., (2022) "Telomerase inhibitors and activators in aging and cancer: A systematic review", Molecular Medicine Reports, 25(158): 1-11.

Jafri et al., (2016) "Roles of telomeres and telomerase incancer, and advances in telomerase-targeted therapies", Genome Medicine, 8(69): 1-18.

Kuznar, (2021) "Imetelstat Has Disease-Modifying Activity in Relapsed/Refractory Myelofibrosis, as Shown by Effect on Telomerase Activity", OncLive, pp. 1-4.

Mascarenhas et al., (2020) "Telomerase activity, telomere length and hTert expression correlate with clinical outcomes in higher-risk myelofibrosis (MF) relapsed/refractory (R/R) to janus kinase inhibitor treated with imetelstat", Abstract 347, Session 634, Presented at American Society of Hematology National Conference.

Santini et al., (2021) "Poster Abstracts", Blood, 138:2598-2600.

Tetsuzo et al., (2003) "Activity of a novel G-quadruplex-interactive telomerase inhibitor, SOT-095, against human leukemia cells: Involvement of ATM-dependent DNA damage response pathways", Oncogene, 22(34):5338-5347.

Yasutaka et al., (2010) "Inhibition of Human Tumor Cell Proliferation by the Telomerase Inhibitor", Telincytologia, 75(2): 177-183.

(56) References Cited

OTHER PUBLICATIONS

Tefferi and Vardiman (2008) "Classification and diagnosis of myeloproliferative neoplasms: The 2008 World Health Organization criteria and point-of-care diagnostic algorithms" Leukemia, 22:14-22.

* cited by examiner

SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tagggttaga caa                                                        13

METHODS OF TREATING MYELODYSPLASTIC SYNDROME

CROSS-REFERENCE TO RELATED APPLICATIONS

This application claims priority to U.S. Provisional Application No. 62/538,315 (filed Jul. 28, 2017), U.S. Provisional Application No. 62/595,329 (filed Dec. 6, 2017), and U.S. Provisional Application 62/685,542 (filed Jun. 15, 2018), the entire contents of each are incorporated by reference herein.

SEQUENCE LISTING

The instant application contains a Sequence Listing, which has been filed electronically in ASCII format and is hereby incorporated by reference in its entirety. Said ASCII copy, created Jun. 19, 2018, is named JBI5134USNP_SL.txt and is 573 bytes in size.

FIELD OF THE INVENTION

The present application relates to treating myelodysplastic syndrome (such as IPSS Low and Intermediate-1 Risk Non-del(5q) MDS) in a patient naive to treatment with a hypomethylating agent, lenalidomide, or both using a telomerase inhibitor.

BACKGROUND OF THE INVENTION

A. Myelodysplastic Syndromes

Myelodysplastic syndromes (MDS) are a group of symptoms that includes cancer of the blood and bone marrow. They also include diseases such as, refractory anemia, refractory anemia with excess blasts, refractory cytopenia with multilineage dysplasia, refractory cytopenia with unilineage dysplasia, and chronic myelomonocytic leukemia. The MDS are a collection of hematological medical conditions that involve ineffective production of the myeloid class of blood cells. In MDS, the immature blood stem cells (blasts) do not become healthy red blood cells, white blood cells, or platelets. The blasts die in the bone marrow or soon after traveling to the blood leaving less room for healthy white cells, red cells, and/or platelets to form in the bone marrow.

MDS primarily affect the elderly and is characterized by anemia and other cytopenias and a high risk of leukemic transformation (Cheson et al., *Blood* 2006; 108:419-425). In clinical practice, MDS are suspected when an otherwise unexplained anemia is associated with other cytopenias, increased mean corpuscular volume, or increased red cell distribution width. Diagnosis involves bone marrow examination and cytogenetic studies. The bone marrow is typically hyperproliferative. Diagnosis is based on demonstration of erythroid, granulocyte, or megakaryocyte dysplasia in 10% or more of informative cells (Vardiman, et al., *Blood* 2009; 114(5):937-951). MDS may progress over time. For example, patients with MDS often develop severe anemia and require frequent blood transfusions. Bleeding and risk of infections also occur due to low or dysfunctional platelets and neutrophils, respectively. In some cases, the disease worsens and the patient develops cytopenias (low blood counts) caused by progressive bone marrow failure. In other cases, the disease transforms into acute myelogenous leukemia (AML). If the overall percentage of bone marrow myeloblasts rises above a particular cutoff (20% for World Health Organization (WHO) and 30% for French-American-British (FAB) subtypes), then transformation to AML is said to have occurred. Limited treatment options exist for patients with lower risk MDS who are relapsed or refractory to erythropoiesis-stimulating agents (ESA).

The standard prognostic tool for assessing MDS is the International Prognostic Scoring System (IPSS), which classifies patients into low, intermediate-1, intermediate-2, and high-risk categories based on several prognostic variables including bone marrow blasts, cytogenetics, and presence of cytopenias. The median survival for these four groups has been estimated at 5.7, 3.5, 1.2, and 0.4 years, respectively. The median times for 25% of patients in these groups to develop AML were 9.4, 3.3, 1.1 and 0.2 years, respectively (Greenberg et al., *Blood* 1997; 89(6):2079-2088). Patients with low and intermediate-1 risk MDS may be referred to as having "lower-risk" disease, whereas those with intermediate-2 and high risk MDS may be referred to as patients with "higher-risk" disease.

In patients aged ≥70 years in Western countries, the incidence of MDS is conservatively estimated approximately at 30 to 40 cases per 100,000 population per year. Due to an aging population, the number of cases of MDS is expected to escalate. Despite the reduced rate of leukemic transformation of lower-risk patients, most patients are affected by anemia and anemia-related symptoms with profound effects on patient-reported outcomes (Almeida et al., *Leukemia Res.* 2017; 52:50-57). Many anemic patients with MDS eventually develop dependence on red blood cell ("RBC") transfusions; evidence suggests that iron overload resulting from chronic RBC transfusion may be a contributing factor in the overall morbidity of the disease (Malcovati et al., *J Clin Oncol* 2005; 23:7594-7603; Malcovati et al., *Haematologica* 2006; 91:1588-1590; Steensma D P., *Mayo Clinic Proc.* 2015; 90(7):969-983). Analysis of retrospective data from 426 patients diagnosed with MDS according to WHO criteria in Italy between 1992 and 2004 showed that a transfusion requirement of 2 units per month reduces the life expectancy of a patient with MDS by approximately 50% (Malcovati et al., Haematologica 2006).

B. Current Treatments for IPSS Low and Intermediate-1 Risk Non-del(5q) MDS

The treatment strategy for MDS is largely based on the IPSS score. In patients classified as IPSS intermediate-2 or high risk (higher-risk MDS), with median survival if untreated of only about 12 months, the treatment goal is modifying the disease course, avoiding progression to AML, and extending survival. In patients classified as IPSS low or intermediate-1 risk (lower-risk MDS), survival is longer, but many patients die from causes other than MDS. Treatment of these patients mainly aims to ameliorate the consequences of cytopenias and transfusions and improve quality of life (Ades et al., *Lancet* 2014; 383(9936): 2239-2252).

Erythropoiesis-Stimulating Agents

For patients with lower-risk non-del(5q) MDS, first-line treatment of anemia often involves the use of erythropoiesis-stimulating agents (ESAs) or other hematopoietic growth factors. High-dose ESAs (e.g. epoetin alfa), with or without granulocyte colony-stimulating factors, have yielded erythroid response rates in the range of 30% to 50% and of median duration 2 years (id.). Key favorable prognostic factors for response to ESAs are low or absent RBC transfusion requirement (<2 packed red blood cell units/month)

and low serum erythropoietin level (≤500 units/L) (Hellstrom-Lindberg et al., *Br J Haematol.* 2003; 120(6):1037-1046). Studies have shown that ESAs have no effect on the risk of progression to higher-risk MDS and AML, and strongly suggest that they may even improve survival in lower-risk MDS compared with RBC transfusion alone (Garcia-Manero et al., *J Clin Oncol.* 2011; 29(5):516-523). In the absence of concomitant progression to higher-risk MDS or AML, patients, who had primary refractoriness to ESA or relapsed within 6 months of response achievement, were observed to have a relatively high risk of AML transformation (23.1%) and short survival (median 3 years), whereas patients, who responded to treatment and relapsed beyond 6 months, had a more favorable outcome after failure with a 9% AML risk at 7 years and a median overall survival of 4.5 years (Kelaidi et al., *Leukemia* 2013; 27(6): 1283-1290).

There is no approved therapy in the United States for patients with lower-risk non-del(5q) MDS who are not responsive to ESA; and treatment options after ESA failure are limited. Most patients with lower-risk MDS will eventually require long-term RBC transfusion, which is often accompanied by iron overload (Ades et al., *Lancet* 2014; Fenaux et al., *Blood* 2013; 121:4280-4286; Steensma et al., *Mayo Clinic* Proc. 2015). Life expectancy for patients with MDS has been shown to be inversely related to RBC transfusion burden (Malcovati et al., *Haematologica* 2006). Patients with chronic anemia despite frequent RBC transfusions may be at risk for associated morbidities (e.g. cardiac failure, falls, fatigue) and lower quality of life (Crawford et al., *Cancer* 2002; 95:888-895).

Hypomethylating Agents

Hypomethylating agents (HMA) (e.g. azacitidine and decitabine) have been approved as treatments for all French-American-British (FAB) subtypes, which includes some lower-risk MDS patients. While these drugs reduce transfusion requirements in higher-risk MDS patients, evidence for improvement of long-term outcomes for lower-risk patients who receive HMAs after ESA failure is absent. In a retrospective study of 1,698 patients with non-del(5q) lower-risk MDS treated with ESAs, patients receiving subsequent treatment with HMAs (n=194) after ESA failure did not experience significant improvement in 5-year overall survival (Park et al., *J Clin Oncol.* 2017; 35(14):1591-1597). According to other reports, in cohorts of patients with lower-risk MDS who are transfusion dependent after ESA failure, azacitidine induces RBC-TI in approximately 14% to 33% of patients (Fili et al., *Clin Cancer Res.* 2013; 19:3297-3308; Thepot et al., *Haematologica.* 2016; 101: 918-925; Tobiasson et al., *Blood Cancer J.* 2014: 4, e189). In view of the limited benefit and observed toxicities (neutropenia, infection), azacitidine cannot be recommended as treatment for these patients (Tobiasson et al., *Blood Cancer J.* 2014).

Lenalidomide

The del(5q) chromosomal abnormality is observed in 10% to 15% of patients with MDS and is associated with a favorable prognosis (Oliva et al., *Ann Hematol.* 2013; 92(1): 25-32). Treatment with lenalidomide results in transfusion independence for approximately two-thirds of such patients (Ades et al., *Lancet* 2014; Fenaux et al., *Blood* 2013; 121(21):4280-4286). In a Phase 3 study, median duration of TI was not reached (median follow-up, 1.55 years) (Fenaux et al., *Blood* 2011; 118(14):3765-3776). Myelosuppression was the most frequently reported Grade 3 or 4 toxicity, and close monitoring of blood counts is required in the first weeks of lenalidomide therapy (id.).

Lenalidomide has also been studied as a treatment for transfusion-dependent non-del(5q) MDS, which represent 85% to 90% of the MDS population. The majority of these subjects do not respond to lenalidomide. Hematologic toxicity (i.e., neutropenia, and thrombocytopenia) was milder than in patients with del(5q) MDS (Loiseau et al., *Exp Hematol.* 2015; 43(8):661-72). Like HMAs, treatment with lenalidomide following ESA failure has not been shown to significantly improve overall survival when used to treat lower-risk non-del(5q) MDS patients (Park et al., *J Clin Oncol.* 2017).

Other Treatment Options

While immunosuppressive therapy is a treatment option for certain lower-risk non-del(5q) patients, no significant effect on transformation-free survival was observed; and adverse events, including hematologic toxicity and associated severe adverse events, such as hemorrhage and infections, have been reported (Almeida et al., *Leukemia Res.* 2017). Allogeneic stem cell transplantation is typically reserved for medically fit higher-risk MDS patients, but may be considered an option for select lower-risk patients, such as those aged <60 to 70 years with IPSS intermediate-1-risk MDS, poor-risk cytogenetics, or persistent blast elevation, if alternative therapeutic options are ineffective (id.).

Limited treatment options are presently available to patients with lower-risk non-del(5q) MDS once first-line treatment with ESAs has failed and patients become dependent on RBC transfusion. Treatment with HMAs or lenalidomide has limited effectiveness in this patient population, and has not shown to have a significant effect on overall survival. Immunotherapy and allogeneic stem cell transplantation are reserved for small, select subgroups of patients with specific disease and patient characteristics. For patients with lower-risk non-del(5q) MDS who are relapsed or refractory to ESA therapy there is a need for a treatment options that delay or avoid transfusion dependence and the associated risks.

BRIEF SUMMARY OF THE INVENTION

The invention provides using telomerase inhibitors, such as e.g. imetelstat, in the treatment of a myelodysplastic syndrome (MDS) in a subject that is naive to treatment with a hypomethylating agent (HMA) or lenalidomide. Accordingly, methods of treating MDS in a subject that is naive to treatment with a HMA, lenalidomide, or both are provided. The subject method includes administering to the subject an effective amount of a telomerase inhibitor. In some cases, the subject is classified as having low or intermediate-1 IPSS risk MDS and/or MDS relapsed/refractory to Erythropoiesis-Stimulating Agent (ESA). In some instances, the telomerase inhibitor is imetelstat sodium.

One embodiment of the invention is a method of treating a myelodysplastic syndrome (MDS) comprising administering to a subject in need thereof an effective amount of a telomerase inhibitor, whereby the subject is naive to treatment with an agent selected from a hypomethylating agent (HMA), lenalidomide, and combination thereof. Another embodiment of the invention is a method of treating a MDS comprising administering to a subject in need thereof an effective amount of a telomerase inhibitor, whereby the subject is naive to treatment with an agent selected from a HMA and lenalidomide. In certain embodiments, the MDS is relapsed or refractory MDS. In one embodiment, the MDS is MDS relapsed/refractory to erythropoiesis-stimulating agent (ESA).

The subject may be transfusion dependent. In one embodiment, the transfusion dependent subject has a transfusion requirement of about four units or more during the 8 weeks prior to the administration of the telomerase inhibitor.

The subject may also be a non-del5q human patient. The subject may also, or alternatively, be classified as being a low or intermediate-1 IPSS risk MDS subject. In certain embodiments, the subject is classified as a low or intermediate-1 IPSS risk MDS subject and is non-del5q. In some embodiments of invention, the MDS is relapsed or refractory MDS and the subject is classified as a low or intermediate-1 IPSS risk MDS subject.

In certain embodiments, the subject is naive to treatment with lenalidomide. In other embodiments, the subject is naive to treatment with HMA. The HMA may be decitabine, azacitidine, or both. Accordingly, in one embodiment, the subject is naive to treatment with decitabine. In another embodiment, the subject is naive to treatment with azacitidine (also known as 5-azacytidine or azacytidine).

Another embodiment of the invention is a telomerase inhibitor, such as e.g. imetelstat, for use in treating a myelodysplastic syndrome (MDS) in a subject naive to treatment with an agent selected from a hypomethylating agent (HMA), lenalidomide, and combination thereof. Alternatively, the subject is naive to treatment with an agent selected from a hypomethylating agent (HMA) and lenalidomide. In one embodiment, the subject is naive to treatment with lenalidomide. In another embodiment, the HMA is selected from decitabine and azacitidine, and the subject is naive to treatment with decitabine or azacitidine. The subject may also be naive to treatment with both decitabine and azacitidine. The MDS may be relapsed or refractory MDS, including MDS relapsed/refractory to erythropoiesis-stimulating agent (ESA). In certain embodiments, the subject is classified as a low or intermediate-1 IPSS risk MDS subject. The subject may also be transfusion dependent, a non-del5q human patient, or both. In alternate embodiments, subject is transfusion dependent subject and has a transfusion requirement of about 4 units or more during the 8 weeks prior to the administration of the telomerase inhibitor. In other embodiments, the subject is classified as a low or intermediate-1 IPSS risk MDS subject and is non-del5q. Alternatively, the MDS is relapsed or refractory MDS and the subject is classified as a low or intermediate-1 IPSS risk MDS subject.

Yet another embodiment of the invention is use of a telomerase inhibitor, such as e.g. imetelstat, to treat a myelodysplastic syndrome (MDS) in a subject naive to treatment with an agent selected from a hypomethylating agent (HMA), lenalidomide, and combination thereof. Such uses also include, use of the telomerase inhibitor in the manufacture of a medicament for treating a myelodysplastic syndrome (MDS) in a subject naive to treatment with an agent selected from a hypomethylating agent (HMA), lenalidomide, and combination thereof. Yet an alternate embodiment of the invention is use of a telomerase inhibitor, such as e.g. imetelstat, to treat a myelodysplastic syndrome (MDS) in a non-del5q human patient. Such uses also include, use of the telomerase inhibitor in the manufacture of a medicament for treating a myelodysplastic syndrome (MDS) in a non-del5q human patient. In certain embodiments of the uses, the subject is naive to treatment with an agent selected from a hypomethylating agent (HMA) and lenalidomide. The HMA may be selected from decitabine and azacitidine. The subject may be naive to treatment with: (a) lenalidomide; (b) decitabine or azacitidine; (c) decitabine and azacitidine; (d) lenalidomide and decitabine or azacitidine, or both. The MDS may be relapsed or refractory MDS, including MDS relapsed/refractory to erythropoiesis-stimulating agent (ESA). In certain embodiments, the subject may classified as a low or intermediate-1 IPSS risk MDS subject and may also be transfusion dependent, a non-del5q human patient, or both. In other embodiments, the subject is transfusion dependent subject and has a transfusion requirement of about 4 units or more during the 8 weeks prior to the administration of the telomerase inhibitor. In additional embodiments, the subject is classified as a low or intermediate-1 IPSS risk MDS subject and is non-del5q. Alternatively, the MDS is relapsed or refractory MDS and the subject is classified as a low or intermediate-1 IPSS risk MDS subject.

The telomerase inhibitor may be imetelstat or imetelstat sodium. In other embodiments, the telomerase inhibitor is imetelstat as well as tautomers, and pharmaceutically acceptable salts thereof. In certain embodiments, imetelstat is administered for 1, 2, 3, 4, 5, 6, 7, 8 or more than 8 dosage cycles, each cycle comprising: intravenous administration of about 7-10 mg/kg imetelstat once every four weeks; intravenous administration of about 7-10 mg/kg imetelstat once weekly for four weeks; intravenous administration of about 2.5-10 mg/kg imetelstat once every three weeks, or intravenous administration of about 0.5-9.4 mg/kg imetelstat once every four weeks. In one embodiment, each dosage cycle comprises intravenous administration of about 7-10 mg/kg imetelstat, alternatively about 7.5 mg/kg, once every four weeks.

In one embodiment of the telomerase inhibitor for use in treating a MDS, the telomerase inhibitor is imetelstat. Similarly, in one embodiment of the use of a telomerase inhibitor, the telomerase inhibitor is imetelstat. In either embodiments, the use may include administration for 1, 2, 3, 4, 5, 6, 7, 8 or more than 8 dosage cycles. In this embodiment, the dosage cycle may comprise: intravenous administration of about 7-10 mg/kg imetelstat once every four weeks; intravenous administration of about 7-10 mg/kg imetelstat once weekly for four weeks; intravenous administration of about 2.5-10 mg/kg imetelstat once every three weeks; or intravenous administration of about 0.5-9.4 mg/kg imetelstat once every four weeks. Accordingly, in one embodiment, each dosage cycle comprises intravenous administration of about 7-10 mg/kg imetelstat once every four weeks. In another embodiment, each dosage cycle comprises intravenous administration of about 7.5 mg/kg imetelstat once every four weeks.

BRIEF DESCRIPTION OF THE DRAWINGS

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

DETAILED DESCRIPTION OF THE INVENTION

Figure 1A:
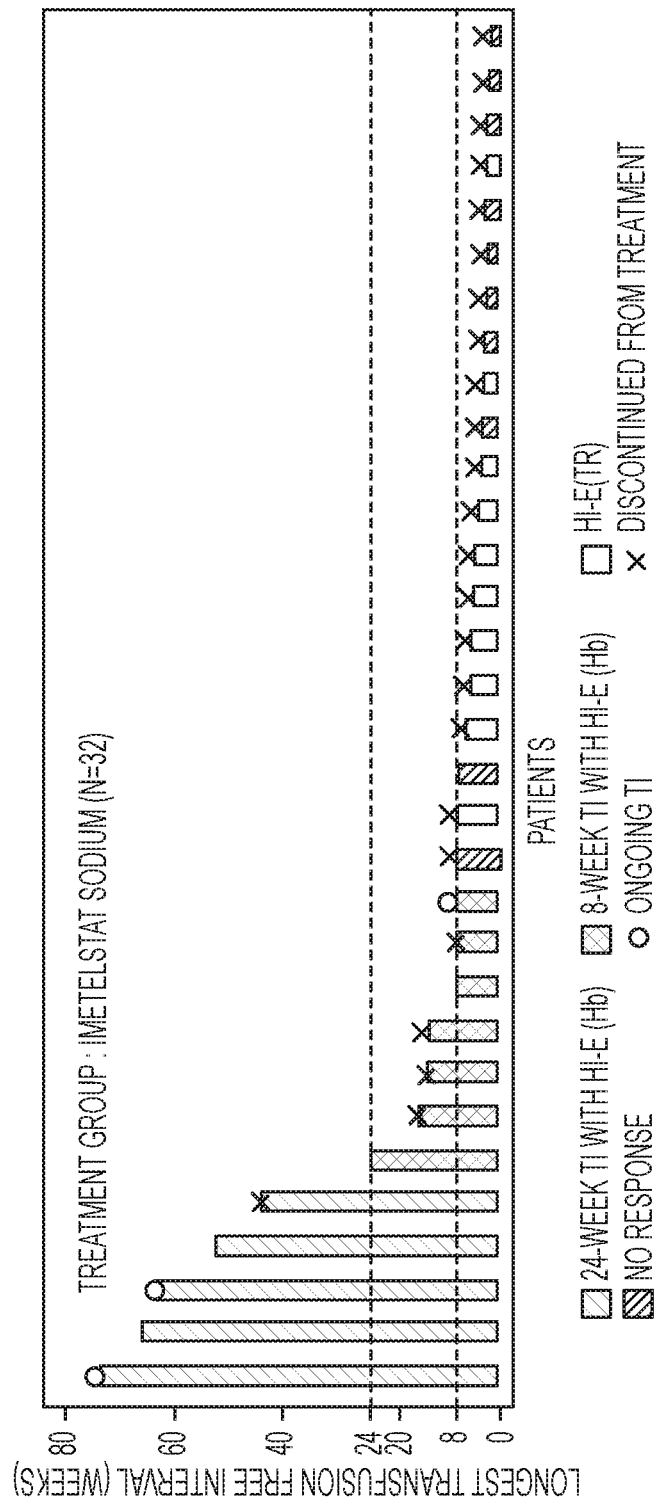
FIGS. 1A and 1B show waterfall plots of the longest transfusion-free interval (FIG. 1A) and absolute change in transfusion amount in the best 8-week interval (FIG. 1B) in a study of imetelstat sodium in red blood cell (RBC) transfusion-dependent (TD) patients as described herein in the experimental section. HI-E=hematologic improvement-erythroid based on a Hb rise of at least 1.5 g/dL above the pretreatment level for at least 8 weeks or reduction of at least 4 units of RBC transfusions/8 weeks compared with the prior RBC transfusion burden (criterion adapted from IWG 2006); HI-E Hb=HI-E with sustained rise in hemoglobin by at least 1.5 g/dL over 8 weeks; TI=transfusion independence; TR=transfusion reduction by at least 4 units over 8 weeks.

This application provides for methods of treating a myelodysplastic syndrome (MDS) in a subject that is naive to treatment with a hypomethylating agent (HMA), lenalidomide or both by administering an effective amount of a telomerase inhibitor, such as imetelstat. In some cases, the subject treated is classified as having: low IPSS risk MDS, intermediate-1 IPSS risk MDS, MDS relapsed to Erythropoiesis-Stimulating Agent (ESA), MDS refractory to MS, or combination thereof. The subject may also be non-del5q. For clarity of disclosure, and not by way of limitation, the detailed description of the invention is divided into subsections that describe or illustrate certain features, embodiments, or applications of the present invention.

A. Definitions

As used herein, the term "about" when referring to a measurable value such as an amount, a temporal duration, and the like, is meant to encompass variations of between ±20% and ±0.1%, preferably ±20% or ±10%, more preferably ±5%, even more preferably ±1%, and still more preferably ±0.1% from the specified value, as such variations are appropriate to perform the disclosed methods.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, and the like; and when the molecule contains a basic functionality, salts of organic or inorganic acids, such as hydrochloride, and the like. Pharmaceutically acceptable salts of interest include, but are not limited to, aluminum, ammonium, arginine, barium, benzathine, calcium, cholinate, ethylenediamine, lysine, lithium, magnesium, meglumine, procaine, potassium, sodium, tromethamine, N-methylglucamine, N,N'-dibenzylethylenediamine, chloroprocaine, diethanolamine, ethanolamine, piperazine, zinc, diisopropylamine, diisopropylethylamine, triethylamine and triethanolamine salts.

The term "salt(s) thereof" means a compound formed when a proton of an acid is replaced by a cation, such as a metal cation or an organic cation and the like. Preferably, the salt is a pharmaceutically acceptable salt. By way of example, salts of the present compounds include those wherein the compound is protonated by an inorganic or organic acid to form a cation, with the conjugate base of the inorganic or organic acid as the anionic component of the salt. Salts of interest include, but are not limited to, aluminum, ammonium, arginine, barium, benzathine, calcium, cesium, cholinate, ethylenediamine, lithium, magnesium, meglumine, procaine, N-methylglucamine, piperazine, potassium, sodium, tromethamine, zinc, N,N'-dibenzylethylene-diamine, chloroprocaine, diethanolamine, ethanolamine, piperazine, diisopropylamine, diisopropylethylamine, triethylamine and triethanolamine salts. It is understood that for any of the oligonucleotide structures depicted herein that include a backbone of internucleoside linkages, such oligonucleotides may also include any convenient salt forms. In some embodiments, acidic forms of the internucleoside linkages are depicted for simplicity. In some instances, the salt of the subject compound is a monovalent cation salt. In certain instances, the salt of the subject compound is a divalent cation salt. In some instances, the salt of the subject compound is a trivalent cation salt. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include for example cis-trans isomers, E and Z isomers, enantiomers, and diastereomers. As to any of the groups disclosed herein which contain one or more substituents, it is understood, of course, that such groups do not contain any substitution or substitution patterns which are sterically impractical and/or synthetically non-feasible. All stereoisomers are intended to be included within the scope of the present disclosure.

A person of ordinary skill in the art would recognize that other tautomeric arrangements of the groups described herein are possible. It is understood that all tautomeric forms of a subject compound are encompassed by a structure where one possible tautomeric arrangement of the groups of the compound is described, even if not specifically indicated.

It is intended to include a solvate of a pharmaceutically acceptable salt of a tautomer of a stereoisomer of a subject compound. These are intended to be included within the scope of the present disclosure.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods, and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates, which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used throughout, "MDS" refers to myelodysplastic syndrome or myelodysplastic syndromes.

B. Treatment

Aspects of the present disclosure include methods of treating a myelodysplastic syndrome (MDS) with a telomerase inhibitor in a subject that is naive to treatment with particular agents, e.g., an agent selected from a hypomethylating agent (HMA) and lenalidomide. A subject is considered to be treatment "naive" if the subject has never undergone the particular treatment for an illness. Treatment of patients with MDS relapsed/refractory to an ESA therapy with imetelstat can improve outcomes, including lower incidence of anemia.

A subject is a mammal in need of treatment for cancer. Generally, the subject is a human patient. In some embodiments of the invention, the subject can be a non-human mammal such as a non-human primate, an animal model (e.g., animals such as mice and rats used in screening, characterization, and evaluation of medicaments) and other mammals. As used herein, the terms patient, subject and individual are used interchangeably.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

In certain instances, the subject method provides an enhanced therapeutic response in those subjects who have not previously been treated with a hypomethylating agent (HMA) or lenalidomide, relative to subjects who were so treated previously. By "enhanced therapeutic response" is meant a statistically significant improvement in a primary and/or secondary endpoint of MDS therapy and/or amelioration of one or more symptoms of MDS (e.g., as described herein), e.g., rate and/or duration of red blood cell (RBC) transfusion-independence (TI), or hematologic improvement (HI) rate relative to an appropriate control. In some cases, the subject methods provide a therapeutic effect of red blood cell (RBC) transfusion-independence (TI), e.g., lasting 4 weeks or longer, such as 5 weeks or longer, 6 weeks or longer, 7 weeks or longer, 8 weeks or longer, 9 weeks or longer, 10 weeks or longer, 12 weeks or longer, 16 weeks or longer, 20 weeks or longer, 24 weeks or even longer. In some instances, time to TI and/or duration of TI is significantly improved. In certain instances, the subject method provides a duration of TI that is 24 weeks or longer, such as 30 weeks or longer, 36 weeks or longer, 42 weeks or longer, 48 weeks or longer, 60 weeks or longer, or even longer.

A hypomethylating agent (HMA) is an agent that inhibits DNA methylation, e.g., by blocking the activity of DNA methyltransferase (DNA methyltransferase inhibitors/DNMT inhibitors). HMAs of interest include, but are not limited to, decitabine (CAS Registry Number: 2353-33-5; 5-aza-2'-deoxycytidine) and azacitidine (CAS Registry Number: 320-67-2, 5-azacytidine). In some instances, the subject is treatment naive to decitabine. In some instances, the subject is treatment naive to azacitidine. In other instances, the subject is treatment naive to both decitabine and azacitidine.

Lenalidomide is a drug that is used to treat a variety of inflammatory disorders and cancers, including multiple myeloma and MDS. Lenalidomide (CAS Registry Number: 191732-72-6; 2,6-Piperidinedione, 3-(4-amino-1,3-dihydro-1-oxo-2H-isoindol-2-yl)-); 3-(4-Amino-1-oxoisoindolin-2-yl)piperidine-2,6-dione) is a derivative of thalidomide. Lenalidomide has various mechanisms of action that provide a broad range of biological activities that can be exploited to treat a variety of hematologic and solid cancers.

Deletion 5q (del5q) refers a chromosomal abnormality found in particular forms of MDS subjects (Adema et al.,

*Haematologica*. 2013 Dec.; 98(12): 1819-1821; Sole et al., *Haematologica*. 2005; 90(9): 1168-78). In some cases of the subject methods, the subject is a human patient who has del5q. In some cases, the subject is a human patient who is non-del5q. A non-del5q subject is a subject that does not have the del5q chromosomal abnormality. In certain cases, the non-del5q subject is human.

In certain instances, the subject has not received prior treatment with either a hypomethylating agent (HMA) or lenalidomide and does not have a del(5q) chromosomal abnormality (e.g., is non-del5q). In certain cases, the non-del5q subject is human.

C. Myelodysplastic Syndrome (MDS)

Myelodysplastic syndrome ("MDS") is a group of diseases that includes cancers of the blood and bone marrow, which in some cases can be characterized by cytopenias resulting from ineffective hemopoiesis. A variety of MDS can be treated using the subject methods, including but are not limited to, diseases such as refractory anemia, refractory anemia with excess blasts, refractory cytopenia with multilineage dysplasia, refractory cytopenia with unilineage dysplasia, chronic myelomonocytic leukemia, MDS with isolated del (5q) and MDS unclassifiable.

MDS is characterized by clonal myeloproliferation arising from malignant progenitor cell clones that have shorter telomeres and multiple clonal genetic abnormalities. Telomerase activity (TA) and expression of human telomerase reverse transcriptase (hTERT) is significantly increased in MDS and may play a role in dysregulated cell growth, leading to continued and uncontrolled proliferation of malignant progenitor cell clones. Higher TA and hTERT as well as shorter telomere length are poor prognostic features for patients with low-risk MDS, leading to shorter overall survival. There are limited treatment options for anemia in lower-risk MDS that has relapsed after or is refractory to ESA therapy. Targeting MDS clones with imetelstat can improve outcomes, including anemia, in patients with MDS relapsed/refractory to an ESA therapy.

In some embodiments, the subject methods find use in alleviating at least one symptom associated with myelodysplastic syndrome, such as, e.g., refractory anemia, refractory anemia with excess blasts, refractory cytopenia with multilineage dysplasia, refractory cytopenia with unilineage dysplasia, and chronic myelomonocytic leukemia. In some embodiments, the symptoms include shortness of breath, fatigue, weakness, fainting, nosebleeds, bruising, bleeding from mouth or gums, bloody stool, petechiae, or stroke.

In some instances, the subject has a relapsed or refractory MDS. "Refractory MDS" refers to patients who still have MDS cells in their bone marrow after treatment with any convenient MDS-related therapy. "Relapsed MDS" refers to patients who have a return of MDS cells in their bone marrow and a decrease in normal blood cells after remission. In certain instances, the subject has MDS relapsed/refractory to Erythropoiesis-Stimulating Agent (ESA). ESAs can increase hemoglobin levels and abolish transfusion dependence for a period of time in some MDS cases. ESAs of interest include but are not limited to erythropoietin-alpha, erythropoietin-beta, and darbepoetin.

In certain embodiments of the subject method, the subject is classified as a low or intermediate-1 IPSS risk MDS subject. Myelodysplastic syndromes (MDS) patients can divided into lower-risk groups (low and intermediate-1 [INT-1] IPSS), in which apoptotic events in the marrow are prevalent and there is a defective response to cytokines (including erythropoietin), and higher-risk groups (intermediate-2 [INT-2] and high IPSS), in which a block in the maturation of marrow progenitors is the principal alteration. In some cases, transfusion dependence is a negative prognostic variable. As such, in certain embodiments of the method, the subject is Red Blood Cell (RBC) transfusion dependent. In some cases, the transfusion-dependent subject has a RBC transfusion requirement of about 4 units or more over 8 weeks; or from 4-14 units over an 8-week period, or about 6 units or more per 8 weeks prior to administration according to the subject method. A unit of packed red blood cells (PRBCs) can be about 300 mL/unit. A unit of Whole blood can be about 450-500 mL/unit.

The International Prognostic Scoring System (IPSS) is a system developed for staging MDS. The IPSS rates 3 factors: the percentage of leukemic blast cells in the bone marrow cells (scored on a scale from zero to 2); chromosome abnormalities, if any, in the marrow cells (scored from zero to 1); and the presence of one or more low blood cell counts (scored as zero or 0.5). Each factor is given a score, with the lowest scores having the best outlook. Then the scores for the factors are added together to make the IPSS score. The IPSS puts people with MDS into 4 groups: low risk; intermediate - 1 risk; intermediate - 2 risk; and high risk.

D. Telomerase Inhibitors

Any convenient telomerase inhibitors can find use in the subject methods. In some embodiments, the telomerase inhibitor is an oligonucleotide with telomerase inhibiting activity, in particular an oligonucleotide as defined in WO 2005/023994 and/or WO 2014/088785, the disclosures of which are herein incorporated by reference in their entirety. In some cases, one or more than one telomerase inhibitor (e.g., two or three telomerase inhibitors) can be administered to a mammal to treat a hematological malignancy.

Imetelstat

In certain embodiments, the telomerase inhibitor is imetelstat, including tautomers thereof and salts thereof, e.g., pharmaceutically acceptable salts. Imetelstat is a novel, first-in-class telomerase inhibitor with clinical activity in hematologic malignancies (Baerlocher et al., NEJM 2015; 373:920-928; Tefferi et al., NEJM 2015; 373:908-919) (shown below):

SEQ ID NO. 1

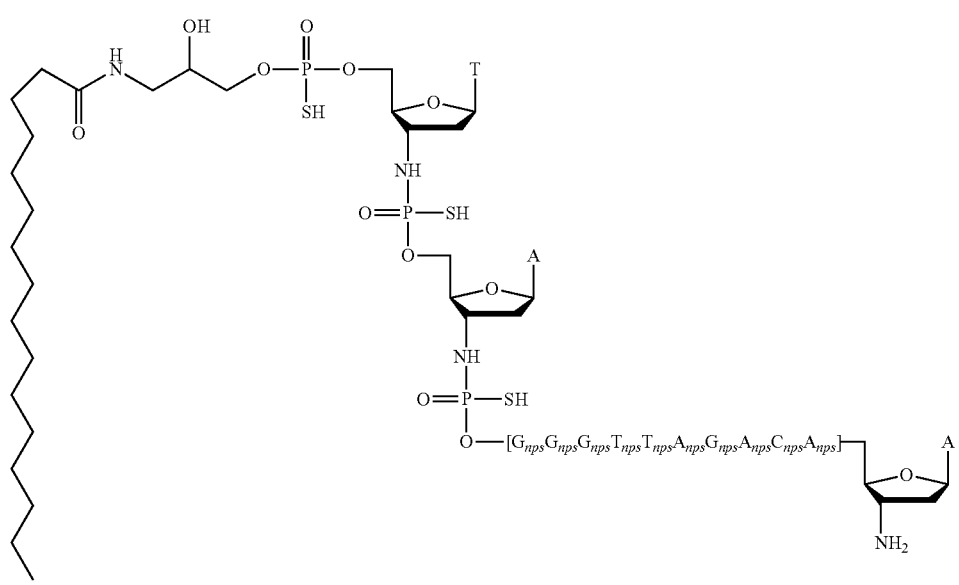

where "nps" represents a thiophosphoramidate linkage —NH—P(=O)(SH)—O—, connecting the 3'-carbon of one nucleoside to the 5'-carbon of the adjacent nucleoside.

In certain instances, the telomerase inhibitor is imetelstat sodium including tautomers thereof. Imetelstat sodium is the sodium salt of imetelstat, which is a synthetic lipid- conjugated, 13-mer oligonucleotide N3'→P5'-thio-phosphoramidate. Imetelstat sodium is a telomerase inhibitor that is a covalently-lipidated 13-mer oligonucleotide (shown below) complimentary to the human telomerase RNA (hTR) template region. The chemical name for imetelstat sodium is: DNA, d(3'-amino-3'-deoxy-P-thio) (T-A-G-G-G-T-T-A-G-A-C-A-A), 5'-[O-[2-hydroxy-3-(hexadecanoylamino)propyl] phosphorothioate], sodium salt (1:13) (SEQ ID NO: 1). Imetelstat sodium does not function through an anti-sense mechanism and therefore lacks the side effects commonly observed with such therapies.

SEQ ID NO. 1
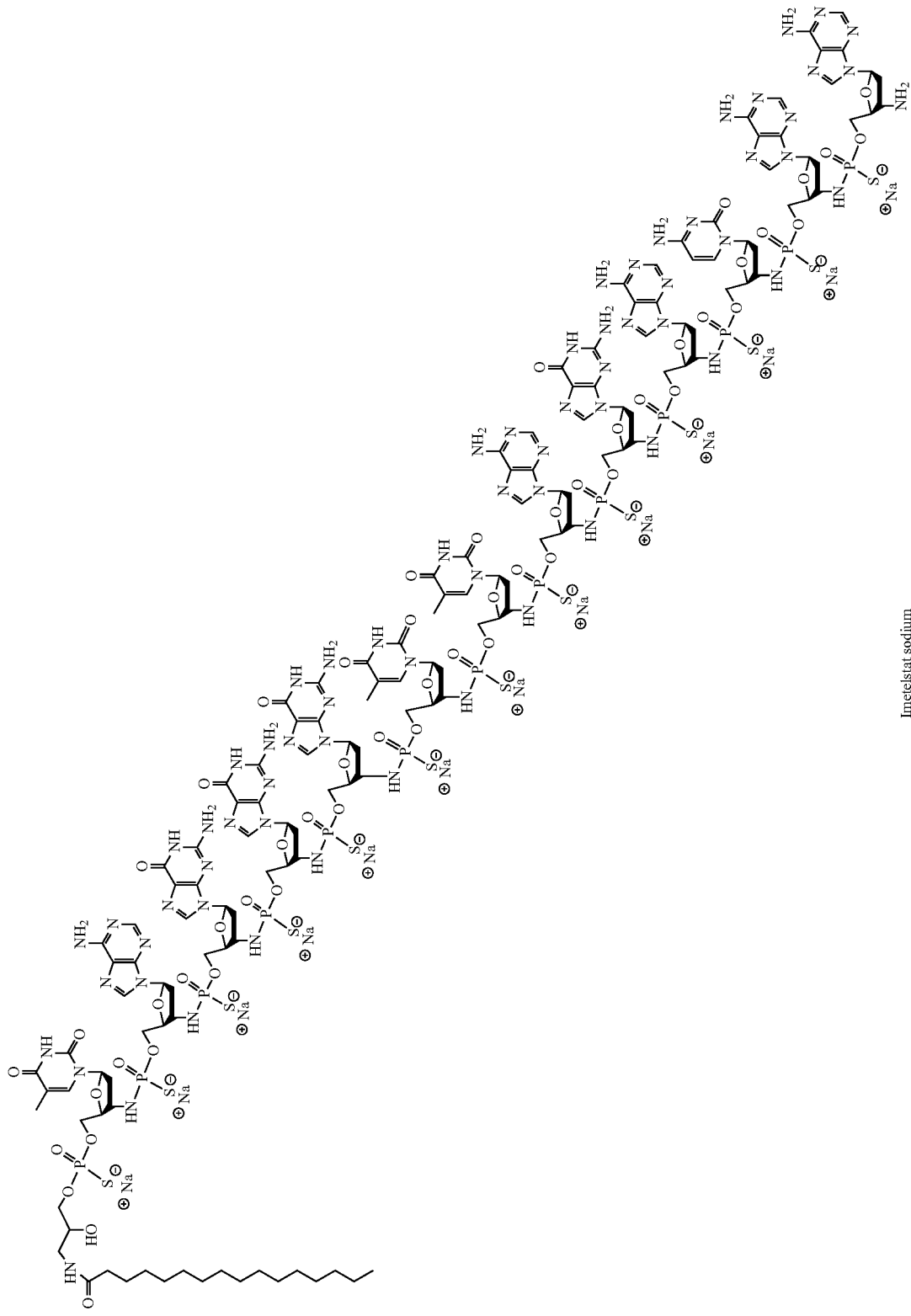
Imetelstat sodium

Unless otherwise indicated or clear from the context, references herein to imetelstat also include tautomers thereof and salts thereof, e.g., pharmaceutically acceptable salts. As mentioned, imetelstat sodium in particular is the sodium salt of imetelstat. Unless otherwise indicated or clear from the context, references herein to imetelstat sodium also include all tautomers thereof.

Imetelstat and imetelstat sodium can be produced, formulated, or obtained as described elsewhere (see e.g. Asai et al., *Cancer Res.*, 63:3931- 3939 (2003), Herbert et al., *Oncogene*, 24:5262-5268 (2005), and Gryaznov, *Chem. Biodivers.*, 7:477-493 (2010)). Unless otherwise indicated or clear from the context, references herein to imetelstat also include salts thereof. As mentioned, imetelstat sodium in particular is the sodium salt of imetelstat.

Imetelstat targets the RNA template of telomerase and inhibits telomerase activity and cell proliferation in various cancer cell lines and tumor xenografts in mice. Phase 1 studies involving patients with breast cancer, non-small-cell lung cancer and other solid tumors, multiple myeloma, or chronic lymphocytic leukemia have provided information on drug pharmacokinetics and pharmacodynamics. A subsequent phase 2 study involving patients with essential thrombocythemia showed platelet-lowering activity accompanied by a significant reduction in JAK2 V617F and CALR mutant allele burdens. Imetelstat sodium is routinely administered intravenously; it is contemplated that in the practice of the subject methods other administration routes also can be used, such as intrathecal administration, intratumoral injection, oral administration and others. Imetelstat sodium can be administered at doses comparable to those routinely utilized clinically. In certain embodiments, imetelstat sodium is administered as described elsewhere herein.

A particular embodiment is according to any one of the other embodiments, wherein imetelstat is limited to imetelstat sodium.

E. Pharmaceutical Compositions

For ease of administration, the telomerase inhibitor (e.g., as described herein) may be formulated into various pharmaceutical forms for administration purposes. In some cases, the telomerase inhibitor is administered as a pharmaceutical composition. The carrier or diluent of the pharmaceutical composition must be "acceptable" in the sense of being compatible with the other ingredients of the composition and not deleterious to the recipients thereof. The pharmaceutical composition may be in unitary dosage form suitable, in particular, for administration orally, rectally, percutaneously, by parenteral injection or by inhalation. In some cases, administration can be via intravenous injection. For example, in preparing the composition in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing the telomerase inhibitor described herein may be formulated in oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired composition. The composition may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the drug described herein in pharmaceutical compositions, it can be advantageous to employ α-, β- or γ-cyclodextrins or their derivatives, in particular hydroxyalkyl substituted cyclodextrins, e.g. 2 hydroxypropyl-β-cyclodextrin or sulfobutyl-β-cyclodextrin. Also, co-solvents such as alcohols may improve the solubility and/or the stability of the telomerase inhibitor in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the telomerase inhibitor described herein, and from 1 to 99.95% by weight, more preferably from 30 to 99.9% by weight, even more preferably from 50 to 99.9% by weight of a pharmaceutically acceptable carrier, all percentages being based on the total weight of the composition.

F. Administration and Administration Regimens

The frequency of administration can be any frequency that reduces the severity of a symptom of a MDS (e.g., as described herein) without producing significant toxicity to the subject. For example, the frequency of administration can be from about once every two months to about once a week, alternatively from about once a month to about twice a month, alternatively about once every six weeks, about once every 5 weeks, alternatively about once every 4 weeks, alternatively about once every 3 weeks, alternatively about once every 2 weeks or alternatively about once a week. The frequency of administration can remain constant or can be variable during the duration of treatment. A course of treatment with a composition containing one or more telomerase inhibitors can include rest periods. For example, a composition containing a telomerase inhibitor can be administered weekly over a three-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the MDS and related symptoms may require an increase or decrease in administration frequency.

An effective duration for administering a composition containing a telomerase inhibitor (e.g., imetelstat or imetelstat sodium) can be any duration that reduces the severity of a symptom of a MDS (e.g., as described herein) without producing significant toxicity to the subject. Thus, the effective duration can vary from one month to several months or years (e.g., one month to two years, one month to one year, three months to two years, three months to ten months, or three months to 18 months). In general, the effective duration for the treatment of a MDS can range in duration from two months to twenty months. In some cases, an effective duration can be for as long as an individual subject is alive. Multiple factors can influence the actual effective duration used for a particular treatment. For example, an effective duration can vary with the frequency of administration, effective amount, use of multiple treatment agents, route of administration, and severity of the MDS and related symptoms.

In certain instances, a course of treatment and the severity of one or more symptoms related to a MDS can be monitored. Any method can be used to determine whether or not the severity of a symptom of a MDS is reduced. For example, the severity of a symptom of a MDS (e.g., as described herein) can be assessed using biopsy techniques.

Telomerase inhibitors as used in the subject methods can be administered at any dose that is therapeutically effective, such as doses comparable to those routinely utilized clinically. Specific dose regimens for known and approved anti-cancer agents (e.g., the recommended effective dose) are known to physicians and are given, for example, in the product descriptions found in the PHYSICIANS' DESK REFERENCE, 2003, 57th Ed., Medical Economics Company, Inc., Oradell, N.J.; Goodman & Gilman's THE PHARMACOLOGICAL BASIS OF THERAPEUTICS" 2001, 10th Edition, McGraw-Hill, New York; and/or are available from the Federal Drug Administration and/or are discussed in the medical literature.

In some aspects, the dose of a telomerase inhibitor, imetelstat sodium, administered to the subject is about 1.0 mg/kg to about 13.0 mg/kg. In other aspects, the dose of a telomerase inhibitor is about 4.5 mg/kg to about 11.7 mg/kg or about 6.0 mg/kg to about 11.7 mg/kg or about 6.5 mg/kg to about 11.7 mg/kg. In some embodiments, the dose of a telomerase inhibitor includes at least about any of 4.7 mg/kg, 4.8 mg/kg, 4.9 mg/kg, 5.0 mg/kg, 5.5 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg.

In some embodiments, the effective amount of a telomerase inhibitor administered to the individual includes at least about any of 1 mg/kg, 2.5 mg/kg, 3.5 mg/kg, 4.7 mg/kg, 5 mg/kg, 6.0 mg/kg, 6.5 mg/kg, 7.5 mg/kg, 9.4 mg/kg, 10 mg/kg, 15 mg/kg, or 20 mg/kg. In some embodiments, the effective amount of a telomerase inhibitor administered to the individual is about any of 1 mg/kg, 2.5 mg/kg, 3.5 mg/kg, 5 mg/kg, 6.5 mg/kg, 7.5 mg/kg, 9.4 mg/kg, 10 mg/kg, 15 mg/kg, or 20 mg/kg. In various embodiments, the effective amount of a telomerase inhibitor administered to the individual includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 7.5 mg/kg, 6.5 mg/kg, 5 mg/kg, 3.5 mg/kg, 2.5 mg/kg, 1 mg/kg, or 0.5 mg/kg of a telomerase inhibitor.

Exemplary dosing frequencies for the pharmaceutical composition including a telomerase inhibitor include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every week, once every 2 weeks, once every 3 weeks, once every 4 weeks, once every 5 weeks, once every 6 weeks, once every 7 weeks or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

Telomerase inhibitors such as imetelstat (e.g., imetelstat sodium) can be administered using any appropriate method. For example, telomerase inhibitors such as imetelstat (e.g., imetelstat sodium) can be administered intravenously once every 4 weeks over a period of time (e.g., one, two, three, four, or five hours). In some embodiments, imetelstat is administered intravenously once weekly over a period of about 2 hours at 7-10 mg/kg. In certain embodiments, imetelstat is administered intravenously once every 3 weeks over a period of about 2 hours at 2.5-7 mg/kg. In an embodiment, imetelstat is administered intravenously for a period of about 2 hours once every 4 weeks at 0.5-5 mg/kg. In an embodiment, imetelstat is administered intravenously once every 3 weeks over a period of about 2 hours at about 2.5-10 mg/kg. Alternatively, imetelstat is administered intravenously for a period of about 2 hours once every 4 weeks at about 0.5-9.4 mg/kg.

In certain embodiments of the method, imetelstat is administered for 1, 2, 3, 4, 5, 6, 7, 8 or more than 8 dosage cycles, each cycle comprising: intravenous administration of about 7-10 mg/kg imetelstat once every four weeks, intravenous administration of about 7-10 mg/kg imetelstat once weekly for four weeks, intravenous administration of about 2.5-10 mg/kg imetelstat once every three weeks, or intravenous administration of about 0.5-9.4 mg/kg imetelstat once every four weeks. In certain instance, each dosage cycle comprises intravenous administration of about 7-10 mg/kg imetelstat once every four weeks. In some cases, each dosage cycle comprises intravenous administration of about 7.5 mg/kg imetelstat about once every four weeks.

In one embodiment of the invention, imetelstat is administered intravenously at a dosage of about 7-10 mg/kg imetelstat once every four weeks following premedication with an antihistamine, corticosteroid, or both. In other embodiments, imetelstat is administered intravenously at a dosage of about 7.5 mg/kg, alternatively from about 7.0 mg/kg to about 7.7 mg/kg, imetelstat once every four weeks following premedication with an antihistamine, corticosteroid, or both.

In certain embodiments, imetelstat is administrated at a dosage about 7.5 mg/kg, alternatively from about 7.0 mg/kg to about 7.7 mg/kg, once every four weeks for at least three cycles and then the dosage is increased. In certain embodiments, the dosage of imetelstat may be increased to about 9.4 mg/kg, alternatively from about 8.8 mg/kg to about 9.6 kg/mg, provided ANC and platelet nadir have not dropped between about $1.5 \times 10^9$/L and about $75 \times 10^9$/L, respectively, and there is no grade ≥3 non-hematological toxicity.

It will be appreciated that treatment for cancer sometimes involves multiple "rounds" or "cycles" of administration of a drug, where each cycle comprises administration of the drug one or more times according to a specified schedule (e.g., every three weeks for three consecutive days; once per week; etc.). For example, anti-cancer drugs can be administered for from 1 to 8 cycles, or for a longer period. When more than one drug (e.g., two-drugs) is administered to a subject, each can be administered according to its own schedule (e.g., weekly; once every three weeks; etc.). It will be clear that administration of drugs, even those administered with different periodicity, can be coordinated so that both drugs are administered on the same day at least some of the time or, alternatively, so the drugs are administered on consecutive days at least some of the time.

As is understood in the art, treatment with cancer therapeutic drugs can be suspended temporarily if toxicity is observed, or for the convenience of the patient, without departing from the scope of the invention, and then resumed.

In certain embodiments, the invention relates to a telomerase inhibitor for use in a method of treating myelodysplastic syndrome (MDS), the method comprising administering to a subject in need thereof an effective amount of a telomerase inhibitor; wherein the subject is naive to treatment with an agent selected from a hypomethylating agent (HMA) and lenalidomide. In other embodiments, the invention relates to a telomerase inhibitor for use in a method of treating myelodysplastic syndrome (MDS), the method comprising administering to a subject in need thereof an effective amount of a telomerase inhibitor; wherein the subject is naive to treatment with an agent selected from a HMA, lenalidomide, and combination thereof.

In certain embodiments, the invention relates to a telomerase inhibitor for use in a method as defined in any of the other embodiments.

G. Exemplary Embodiments

Exemplary embodiments of the methods of treating MDS of the invention, which involve administering to a subject in need thereof an effective amount of a telomerase inhibitor whereby the subject is naive to treatment with an agent selected from a hypomethylating agent (HMA) and lenalidomide are shown in Table A below.

Exemplary embodiments include using any of the telomerase inhibitors in Table A to treat any one of the types of MDS shown in Table A in any one of the subjects shown in Table A, whereby the subject is naïve to any one of the treatments shown in Table A. In certain embodiments, one of the administration regimens described in Table A is used. In other embodiments, the methods may be used to treat any one of the types of MDS shown in Table A in any one of subjects shown in Table A using imetelstat (imetelstat sodium), whereby the subject is naïve to any one of the treatments shown in Table A. When imetelstat (imetelstat sodium) is used, any of the administration regimens shown in Table A may be used.

TABLE A

| | Exemplary embodiments of the invention |
|---|---|
| Type of MDS | MDS |
| | Relapsed or refractory MDS |
| | Relapsed MDS |
| | Refractory MDS |
| | MDS relapsed/refractory to erythropoiesis-stimulating agent (ESA) (e.g. erythropoietin-alpha, erythropoietin-beta, darbepoetin, or combination thereof). |
| Subject | low or intermediate-1 IPSS risk MDS subject |
| | low or intermediate-1 IPSS risk MDS subject and transfusion dependent |
| | low or intermediate-1 IPSS risk MDS subject and transfusion dependent with a transfusion requirement of about 4 units or more during the 8 weeks prior to the administration of the telomerase inhibitor |
| | transfusion dependent e.g. transfusion dependent with a transfusion requirement of about 4 units or more during the 8 weeks prior to the administration of the telomerase inhibitor |
| | low or intermediate-1 IPSS risk MDS subject and non-del5q |
| | low or intermediate-1 IPSS risk MDS subject, non-del5q, and transfusion dependent |
| | low or intermediate-1 IPSS risk MDS subject, non-del5q, and transfusion dependent with a transfusion requirement of about 4 units or more during the 8 weeks prior to the administration of the telomerase inhibitor |

TABLE A-continued

Exemplary embodiments of the invention

| | |
|---|---|
| | non-del5q |
| | non-del5q and transfusion dependent |
| | non-del5q and transfusion dependent with a transfusion requirement of about 4 units or more during the 8 weeks prior to the administration of the telomerase inhibitor |
| Subject naive to treatment with | Hypomethylating agent (e.g. decitabine or azacitidine) |
| | Hypomethylating agent (e.g. decitabine or azacitidine) and lenalidomide |
| | decitabine |
| | azacitidine |
| | azacitidine and decitabine |
| | lenalidomide |
| | lenalidomide and decitabine |
| | lenalidomide and azacitidine |
| | lenalidomide, azacitidine, and decitabine |
| Telomerase inhibitor | Any suitable inhibitor or imetelstat (imetelstat sodium) |
| Administration | Administration of telomerase inhibitor for 1, 2, 3, 4, 5, 6, 7, 8 or more than 8 dosage cycles |
| | Administration of imetelstat (imetelstat sodium) for 1, 2, 3, 4, 5, 6, 7, 8 or more than 8 dosage cycles, each cycle comprising: (a) intravenous administration of about 7-10 mg/kg imetelstat once every four weeks; (b) intravenous administration of about 7-10 mg/kg imetelstat once weekly for four weeks; (c) intravenous administration of about 2.5-10 mg/kg imetelstat once every three weeks; or (d) intravenous administration of about 0.5-9.4 mg/kg imetelstat once every four weeks. |
| | Administration of imetelstat (imetelstat sodium) for 1, 2, 3, 4, 5, 6, 7, 8 or more than 8 dosage cycles, each cycle comprises intravenous administration of about 7-10 mg/kg of imetelstat (imetelstat sodium) once every four weeks |
| | Administration of imetelstat (imetelstat sodium) for 1, 2, 3, 4, 5, 6, 7, 8 or more than 8 dosage cycles, each cycle comprises intravenous administration of about 7.5 mg/kg imetelstat of imetelstat (imetelstat sodium) once every four weeks |

The following examples are offered by way of illustration and not by way of limitation.

EXAMPLES

Example 1: Efficacy and Safety of Imetelstat in Transfusion-Dependent (TD) Patients with International Prognostic Scoring System (IPSS) Low/Intermediate-1 Risk Myelodysplastic Syndromes that are Relapsed/Refractory to Erythropoiesis-Stimulating Agent (ESA) Treatment (IMerge™)

Introduction

IMerge™: ongoing 2-part, global, study of imetelstat sodium in red blood cell (RBC) transfusion-dependent (TD) patients, ESA-relapsed/refractory, and lower risk MDS. Part 1 consists of an open-label, single-arm design with imetelstat sodium monotherapy. This example provides safety and efficacy findings from 32 patients enrolled in Part 1. A subgroup analysis of patients naive to lenalidomide and hypomethylating agent (HMA) treatment and without del (5q) is also presented. The results suggest improved efficacy among these patients.

Methods

Eligibility: The eligibility requirements for the study were as follows:
Adults diagnosed with MDS; International Prognostic Scoring System (IPSS) Low or Int-1
Transfusion Dependence (TD), defined as a red blood cell (RBC) transfusion requirement of ≥4 units over 8 weeks prior to study entry.
ESA relapsed or refractory following at least 8 weeks of weekly epoetin alfa 40,000 U or darbepoetin alfa 150 mcg (or equivalent) or serum erythropoietin (sEPO) >500 mU/mL
Any prior therapy (including lenalidomide or HMAs) allowed. Patients with the del(5q) karyotype were allowed to enter irrespective of prior treatment.
Eastern Cooperative Oncology Group (ECOG) score 0-2.
Absolute neutrophil count (ANC) ≥1.5×10$^9$/L and platelets ≥7 5×10$^9$/L independent of growth factor or transfusion support.
Liver function tests: AST, ALT and ALP ≤2.5 times the upper limit of normal (x ULN), total bilirubin ≤3×ULN and direct bilirubin ≤2×ULN (unless due to Gilbert's syndrome).

Treatment: Imetelstat sodium was administered as a 2-hour IV infusion every 4 weeks at a starting dose of 7.5 mg/kg, following premedication with an antihistamine and corticosteroid. Dose escalation to 9.4 mg/kg was permitted for insufficient response after at least 3 cycles at the initial dose, provided that ANC and platelet nadirs had not dropped below 1.5×10$^9$/L and 75×10$^9$/L, respectively, and no grade ≥3 non-hematological toxicity. Supportive care, including transfusion and myeloid growth factors as clinically indicated, was permitted.

Endpoints and Analysis:
Primary endpoint: rate of RBC transfusion-independence (TI) lasting >8 weeks.
Key secondary endpoints:
Safety;
Rate of ≥24-week TI;
Time to and duration of TI;
Hematologic improvement (HI) rate; and
Rate of complete response (CR) and partial response (PR) per International Working Group (IWG).

Results

Patients

Baseline median RBC transfusion burden, 6 units/8 weeks (range: 4-14)

The baseline characteristics are shown in Table 1 below. The following abbreviations are used in Table 1: Eastern Cooperative Oncology Group Performance Status Score of 0-1 ("ECOG PS 0-1"); refractory anemia with ringed sideroblasts ("RARS"); or refractory cytopenia with multi-lineage dysplasia and ringed sideroblasts ("RCMD-RS").

TABLE 1

Baseline characteristics (N = 32)

| | |
|---|---|
| Median age (range), y | 68.5 (46-83) |
| Male, n (%) | 16 (50) |
| ECOG PS 0-1 (%) | 29 (91) |
| IPSS risk, n (%) | |
| Low | 19 (59) |
| Intermediate-1 | 13 (41) |
| Karyotype | |
| Normal | 17 (53) |
| Any Abnormality | 11 (34) |
| del(5q) | 7 (22) |
| Unknown (missing or no growth) | 4 (13) |
| WHO category, n (%) | |
| RARS/RCMD-RS | 16 (50) |
| All others | 16 (50) |
| sEPO >500 mU/mL, n (%) | 13* (43) |
| Prior ESA | 28 (88) |
| Prior lenalidomide, n (%) | 12 (38) |
| Prior decitabine or azacitidine | 8 (25) |
| Naive to lenalidomide and HMA and non-del (5q), n (%) | 13 (41) |

*Of 30 patients with sEPO levels reported

Key hematologic criteria: ANC=1,500 and PLT=75,000. Based on the baseline RBC transfusion burden, this was a heavily transfused group of patients.

Results (First Data Snapshot)

Exposure

Median follow-up for this analysis: 66.1 weeks

Median number of treatment cycles: 6.5 (range: 1-20 cycles)

Sixteen patients (50%) had dose reductions and 19 patients (59%) had cycle delays due to adverse events Seven patients had imetelstat sodium dose escalation to 9.4 mg/kg

Efficacy

Table 2 below shows key efficacy outcomes.

TABLE 2

Key Efficacy Outcomes

| Outcomes | All treated (N = 32) | Lenalidomide and HMA naive and non-del(5q) (n = 13) |
|---|---|---|
| Rate of ≥8-week TI, n (%) | 12* (38) | 7 (54) |
| Mean relative reduction from baseline transfusion burden (%) | −64 | −71 |
| Rate of ≥24-week TI, n (%) | 5 (16) | 4 (31) |
| Median time to onset of TI, weeks | 8.1 | 8.3 |
| Median duration of TI, weeks | 23.1 | 42.9 |
| Erythroid HI rate, n (%) | 20† (63) | 9† (69) |
| CR + mCR + PR (per IWG), n (%) | 4 (13) | 3 (23) |

*Results are based on the Oct. 16, 2017 data snapshot("first data snapshot"), at which one ≥ 8-week TI had not been fully confirmed based on communication with investigator
†Includes patients with a transfusion reduction of ≥4 units during the best 8-week on-study interval, as well as those with a hemoglobin increase from pretreatment level.

The primary endpoint of RBC TI lasting ≥8-weeks was achieved in 12/32 (38%) patients.

Figure 1B:
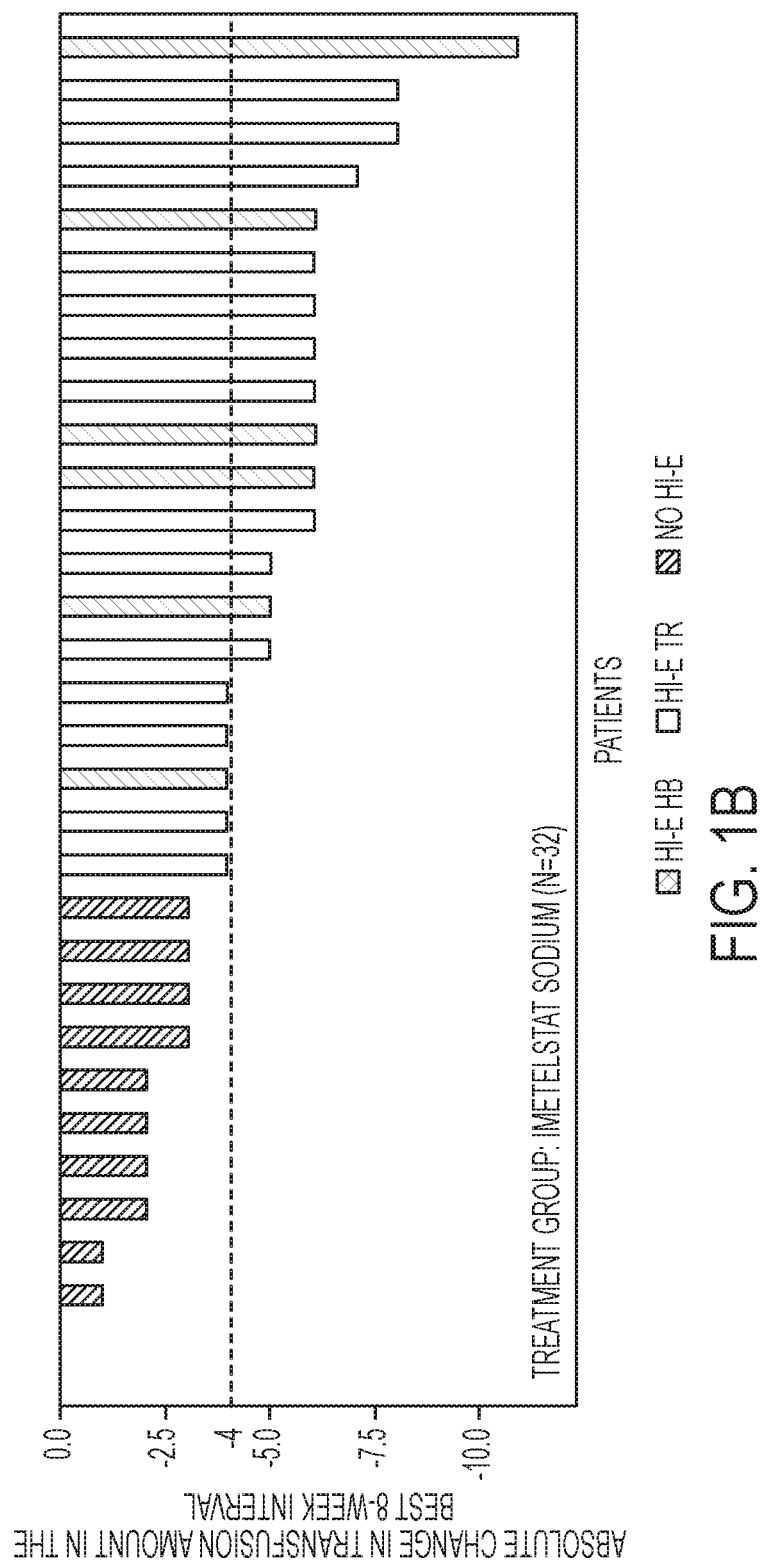
Figure 2:
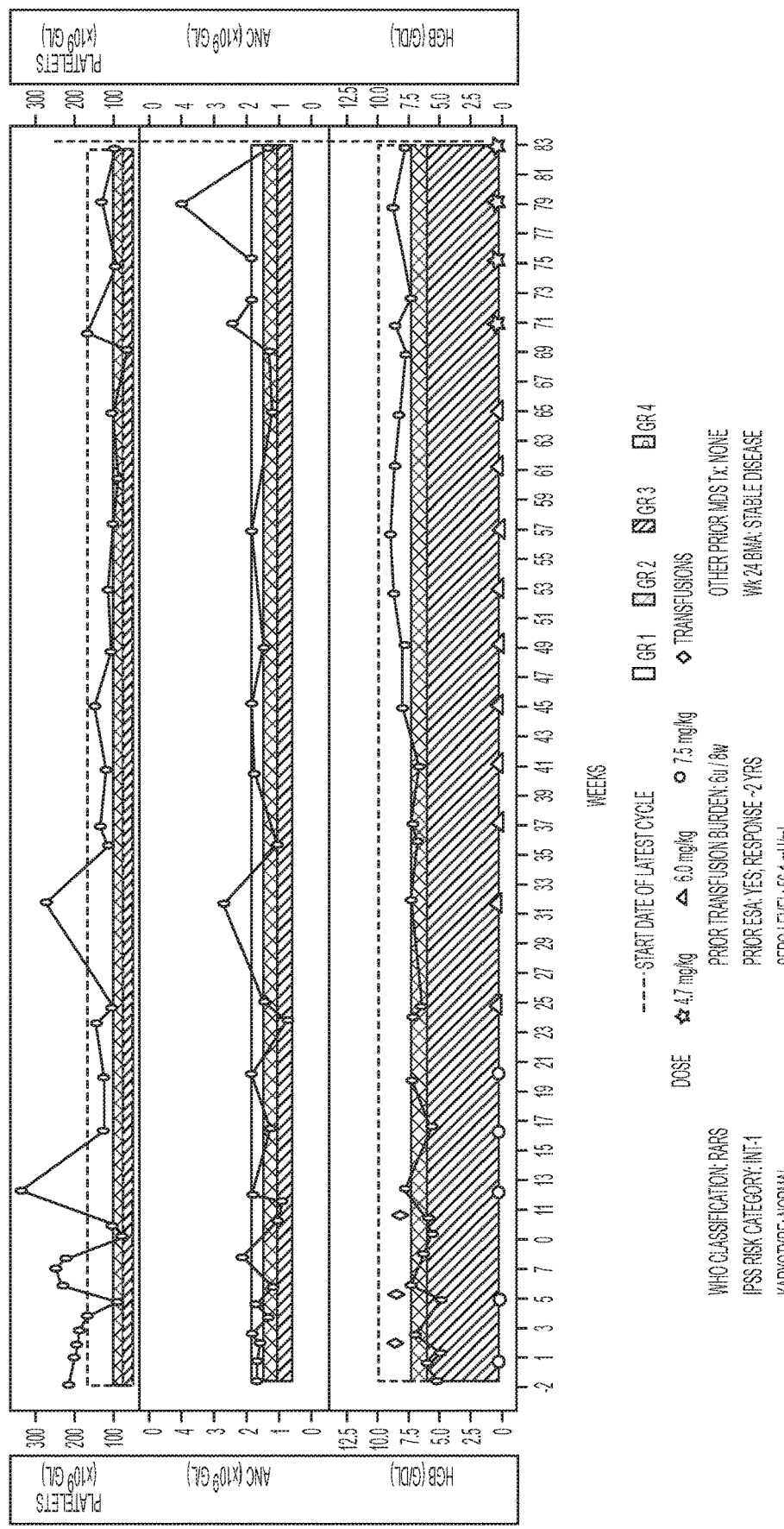
FIG. 2 shows a hematology and imetelstat sodium administration timeline for an exemplary 24-week transfusion independent (TI) responder.

5/32 (16%) achieved 24-week TI (see FIGS. 1A, 1B and FIG. 2). These patients also achieved sustained hemoglobin increases by at least 1.5 g/dL over 8 weeks (HI-E Hb) (HI-E Hb=HI-E with sustained rise in hemoglobin by at least 1.5 g/dL over 8 weeks). The patients' duration of TI (65.1 weeks) exceeded one year.

20/32 patients (63%) had an erythroid hematologic improvement (HI) (see FIG. 1A and FIG. 1B).

In the subset of patients who were naive to lenalidomide and HMAs and who lacked del(5q), 8-week and 24-week TI rates were 54% and 31%, respectively (higher than in the overall population) and the erythroid HI rate was 69% (similar to that reported in the overall population). Complete Response (CR) and marrow CR (mCR) were each reported for 2 patients and there were no Partial Responses (PRs), for a CR+PR+mCR rate of 13%.

One CR and both mCR were in the subset of patients who were naive to lenalidomide and HMAs and who lacked del(5q). 8-week TI did not differ based on the presence of ringed sideroblasts (RS): 38% (6/16) for RS+and 38% (6/16) for RS-. Response appeared to be independent of sEPO level; of 30 patients with baseline sEPO level reported: 41% (7/17) with sEPO level ≤500 mU/L achieved ≥8-week TI; and 38% (5/13) with sEPO level >500 mU/L achieved ≥8-week TI.

Safety

Cytopenias, particularly neutropenia and thrombocytopenia, were the most frequently reported adverse events overall and in the subset who were naive to lenalidomide and HMAs and lacked del(5q) (see Table 3 below). This subset of patients had a lower incidence of grade ≥3 neutropenia relative to the overall population but similar grade ≥3 thrombocytopenia (see Table 4 below). In most cases, grade ≥3 cytopenias were reversible within 4 weeks without clinical sequelae, and patients were able to continue imetelstat sodium treatment after dose modification.

1 patient (of 22 with neutropenia) experienced neutropenic fever and 2 patients (of 18 with thrombocytopenia) had grade 3 thrombocytopenia concurrent with grade 1 bleeding events that were both considered related to imetelstat sodium; these events recovered without sequelae. 28 patients (88%) had liver function test (LFT) elevations by at least one grade. These events were generally grade 1 or 2 and reversible. Four patients (including 3 in the subset of patients who were naive to lenalidomide and HMAs and who lacked del[5q]) had grade 3 worsening of aspartate aminotransferase (AST) and/or alanine aminotransferase (ALT), and 1 of these patients had grade 3 worsening of bilirubin; all of which were reversible.

Table 3 shows the most common treatment emergent adverse events. Table 4 shows the maximum grade change in cytopenias from baseline.

TABLE 3

Most Common Treatment-Emergent Adverse Events
(≥10% of Patients in All Treated Patients)

| | All Treated (N = 32) | Lenalidomide and HMA naive and non-del(5q) (n = 13) |
|---|---|---|
| Patients with ≥1 treatment emergent adverse events ("AEs"), n (%) | 31 (97) | 12 (92) |
| Neutropenia | 22 (69) | 7 (54) |
| Thrombocytopenia | 18 (56) | 8 (62) |
| Headache | 8 (25) | 2 (15) |
| Alanine aminotransferase ("ALT") increased | 6 (19) | 3 (23) |
| Aspartate aminotransferase ("AST") increased | 5 (16) | 3 (23) |
| Leukopenia | 5 (16) | 2 (15) |
| Muscle spasms | 5 (16) | 2 (15) |
| Anemia | 4 (13) | 2 (15) |
| Asthenia | 4 (13) | 4 (31) |
| Constipation | 4 (13) | 2 (15) |
| Cough | 4 (13) | 1 (8) |
| Diarrhea | 4 (13) | 1 (8) |
| Dyspnea | 4 (13) | 2 (15) |
| Influenza like illness | 4 (13) | 1 (8) |
| Nausea | 4 (13) | 2 (15) |
| Peripheral edema | 4 (13) | 2 (15) |
| Viral URI | 4 (13) | 4 (31) |

TABLE 4

Maximum Grade Change in Cytopenias From Baseline

| | All Treated (N = 32) | Lenalidomide and HMA naive and non-del(5q) (n = 13) |
|---|---|---|
| Neutrophils, n (%) | | |
| No worsening | 4 (13) | 3 (23) |
| 1 | 3 (9) | 1 (8) |
| 2 | 4 (13) | 2 (15) |
| 3 | 8 (25) | 2 (15) |
| 4 | 13 (41) | 5 (38) |
| Platelets, n (%) | | |
| No worsening | 7 (22) | 3 (23) |
| 1 | 2 (6) | 1 (8) |
| 2 | 7 (22) | 2 (5) |
| 3 | 10 (31) | 5 (38) |
| 4 | 6 (19) | 2 (15) |

Results in Table 4 are based on the first data snapshot.

Results (Second Data Snapshot)

Exposure

Median follow-up for this analysis: 95 weeks

Median number of treatment cycles: 6.5 (range: 1-28 cycles)

Sixteen patients (50%) had dose reductions and 19 patients (59%) had cycle delays Seven patients had imetelstat sodium dose escalation to 9.4 mg/kg Efficiency Table 5 below shows key efficiency outcomes at the second data snapshot.

TABLE 5

Key Efficacy Outcomes

| Parameters | All Treated (N = 32) | Lenalidomide and HMA naive and non-del(5q) (n = 13) |
|---|---|---|
| Rate of 8-week TI, n (%) | 11 (34) | 7 (54) |
| Rate of 24-week TI, n (%) | 5 (16) | 4 (31) |
| Median time to onset of TI (range), weeks | 8.0 (0.1-33.1) | 8.3 (0.1-33.1) |
| Median duration of TI (range), weeks | 23.1 (8-105) | 42.9 (8-105) |
| Rate of transfusion reduction (HI-E), n (%) | 19 (59) | 9 (69) |
| Mean relative reduction of RBC transfusion burden from baseline, % | −60 | −71 |
| CR + marrow CR + PR (per IWG), n (%) | 6 (19) | 4 (31) |

*Results are based on the May 10, 2018 data snapshot ("second data snapshot")
†Includes patients with a transfusion reduction of ≥ 4 units during the best 8-week on-study interval, as well as those with a hemoglobin increase from pretreatment level.

Maximum duration of follow-up from responding patient was 115 weeks or 26 months.

Among the seven subjects who had dose escalation, one subject reached 8-week TI and three subjects reached HI-E. The median number of treatment cycles for subgroup was 8 cycles. Median duration of therapy overall and subgroup was 24 weeks and 29 weeks, respectively.

Figure 3A:
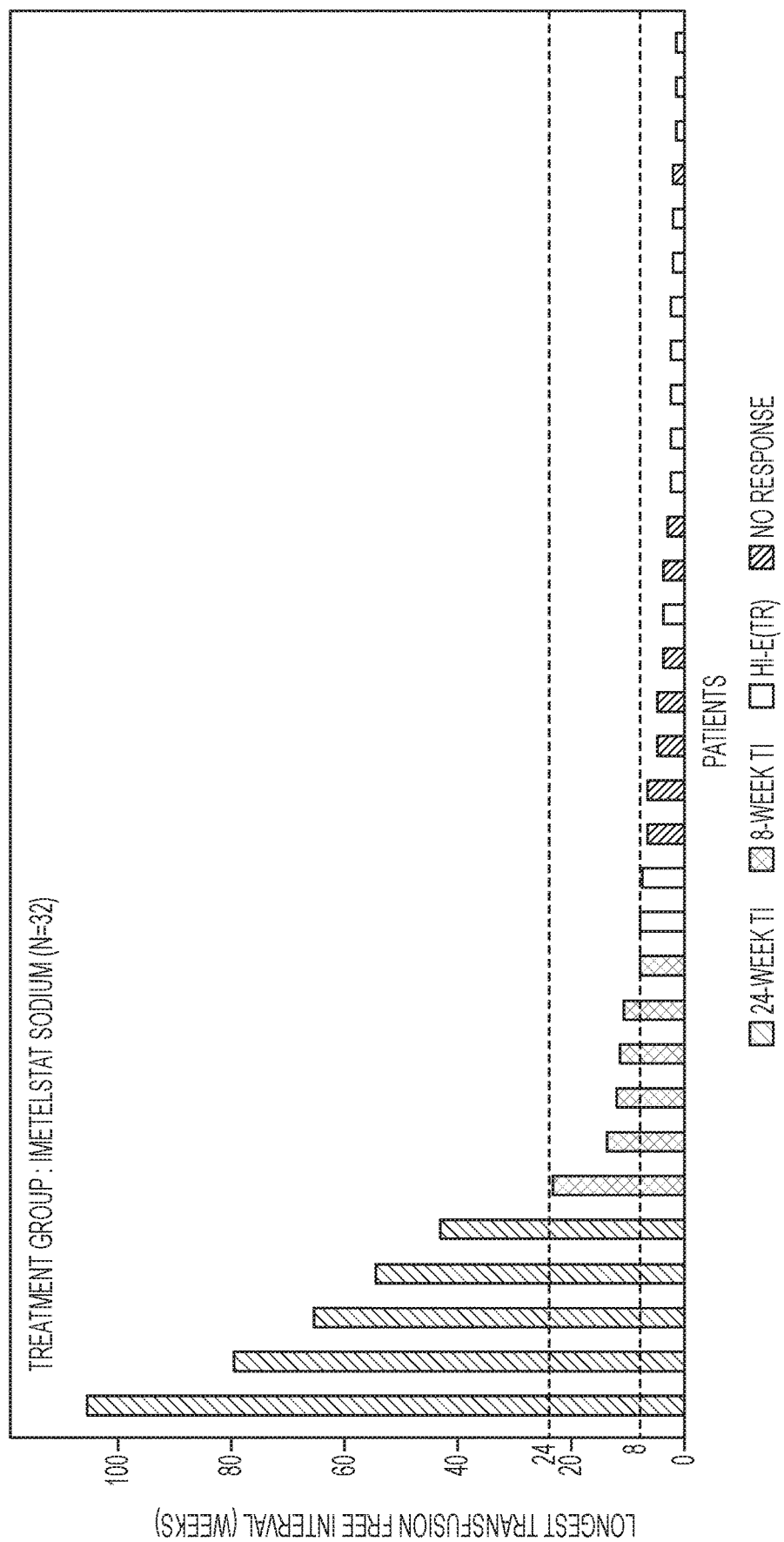
FIGS. 3A and 3B show waterfall plots of the longest transfusion-free interval (FIG. 3A) and absolute change in transfusion amount in the best 8-week interval (FIG. 3B) in a study of imetelstat sodium in red blood cell (RBC) transfusion-dependent (TD) patients as described herein in the experimental section. HI-E =hematologic improvement-erythroid based on a Hb rise of at least 1.5 g/dL above the pretreatment level for at least 8 weeks or reduction of at least 4 units of RBC transfusions/8 weeks compared with the prior RBC transfusion burden (criterion adapted from IWG 2006); TI=transfusion independence; TR=transfusion reduction by at least 4 units over 8 weeks.

FIG. 3A shows the longest transfusion free interval at the second data snapshot. Three of the five patients at 24-week TI are still on treatment. The data shown in FIG. 3A are summarized in Table 6 below:

TABLE 6

Longest Transfusion-Free Interval

| Parameters | All Treated (N = 32) |
|---|---|
| Rate of 8-week TI, n (%) | 11 (34) |
| Rate of 24-week TI, n (%) | 5 (16) |
| Median time to onset of TI (range), weeks | 8.0 (0.1-33.1) |
| Median duration of TI (range), weeks | 23.1 (8-105) |

Figure 3B:
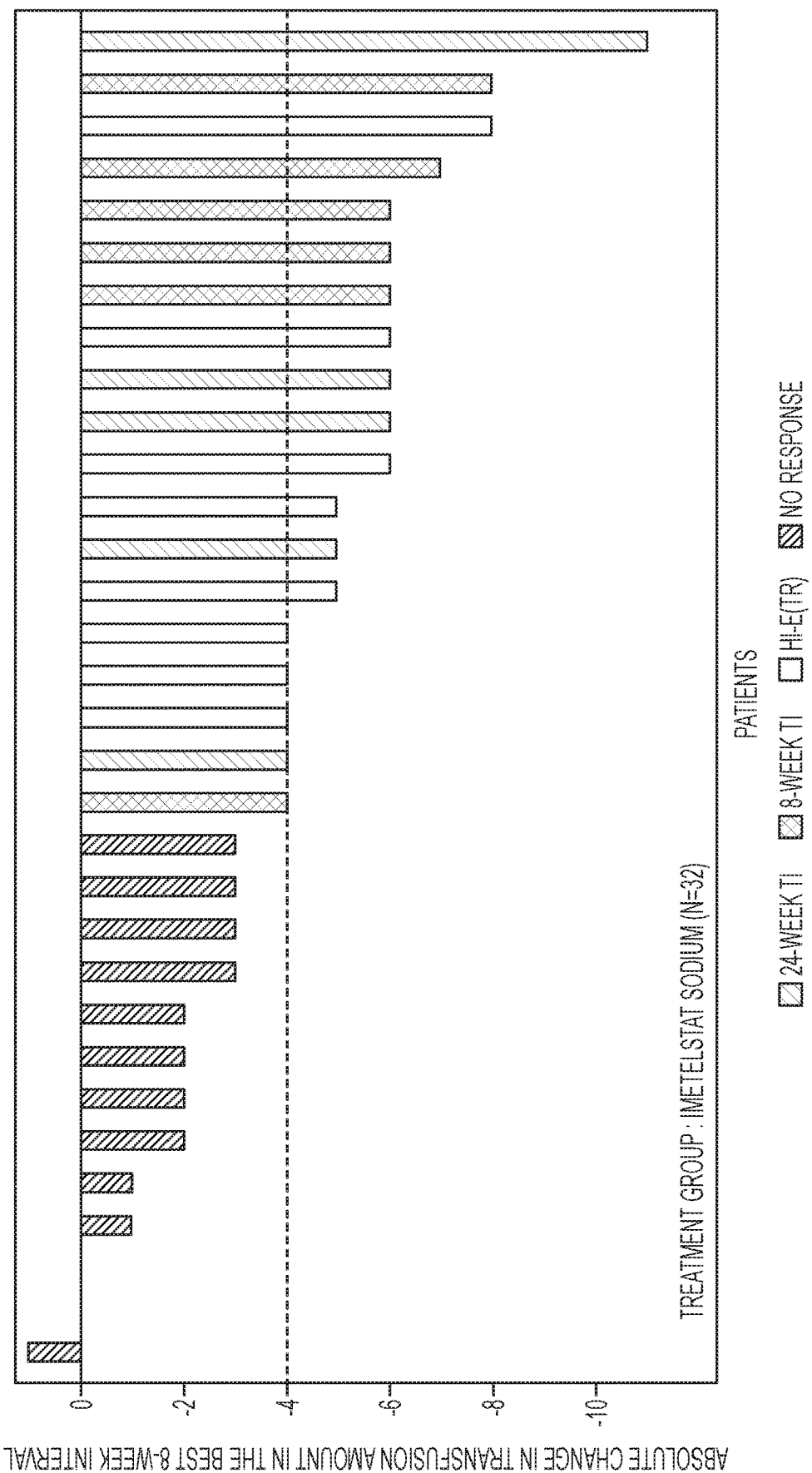

FIG. 3B shows the absolute change in transfusion amount in the best 8-week interval. One patient with transfusion burden of 10 went down to 0. Patients not achieving TI (HI-E (TR)) had some fairly meaningful reductions in transfusion burden. The data shown in FIG. 3B are summarized in Table 7 below:

TABLE 7

Absolute Change in Transfusion Amount in the Best 8-Week Interval

| Parameters | All Treated (N = 32) |
|---|---|
| Rate of transfusion reduction (HI-E), n (%) | 19 (59) |
| Mean relative reduction of RBC transfusion burden from baseline, % | −60 |

Figure 4:
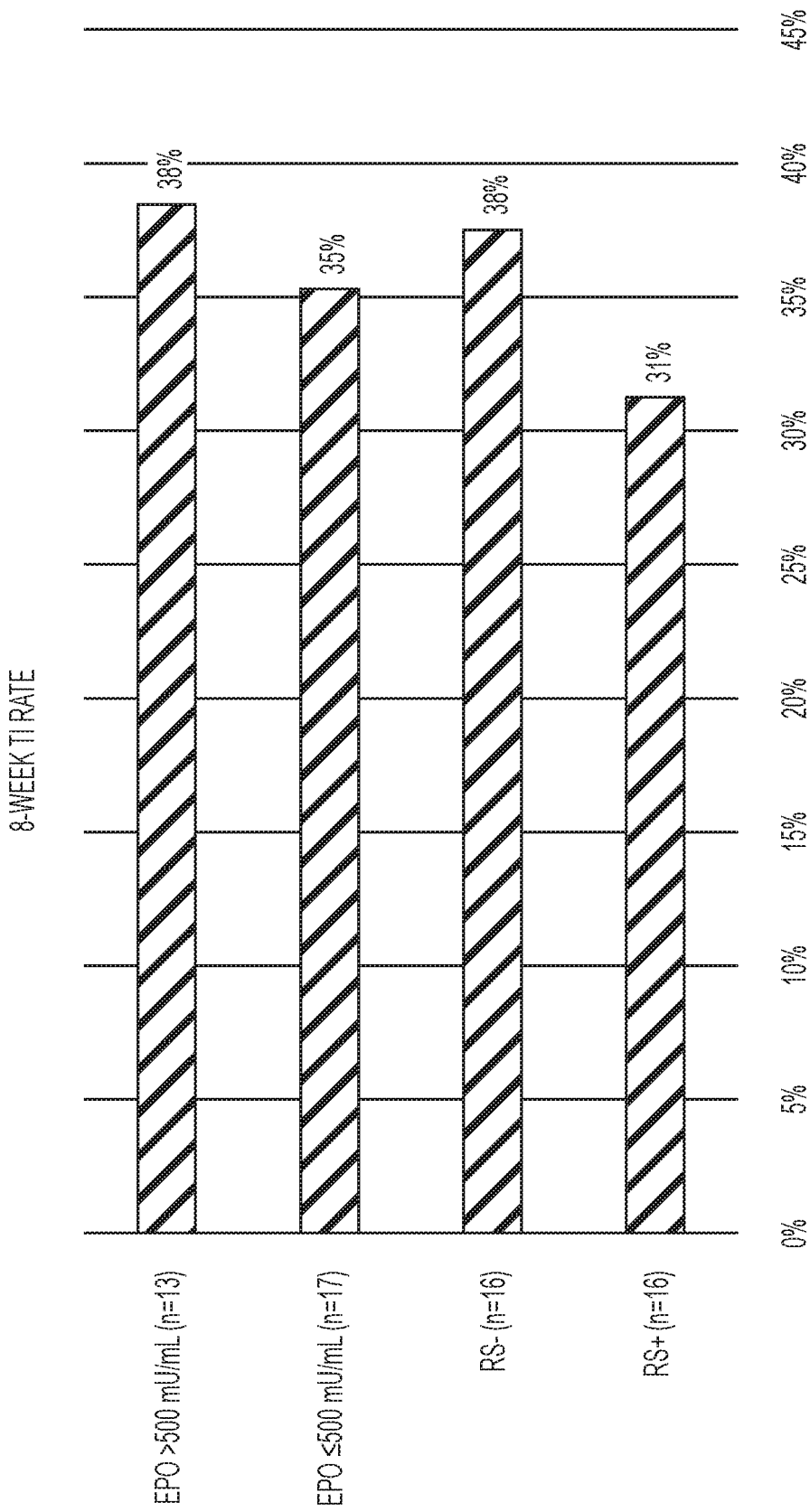
FIG. 4 shows the Efficacy Results in EPO and RS Subgroups.
Figure 5:
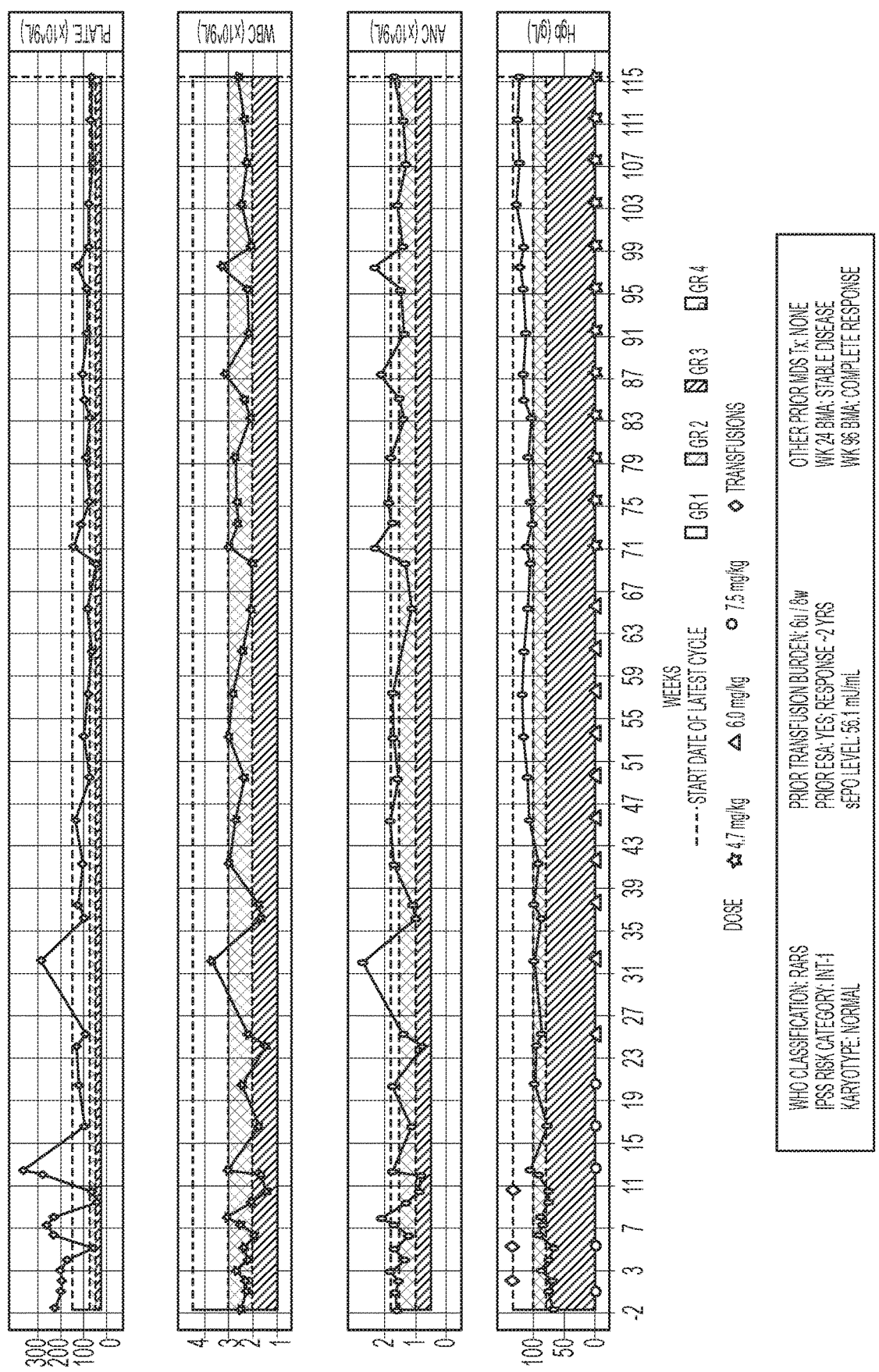
FIG. 5 shows a hematology and imetelstat sodium administration timeline for up to 115 weeks for an exemplary 24-week transfusion independent (TI) responder.
Figure 6:
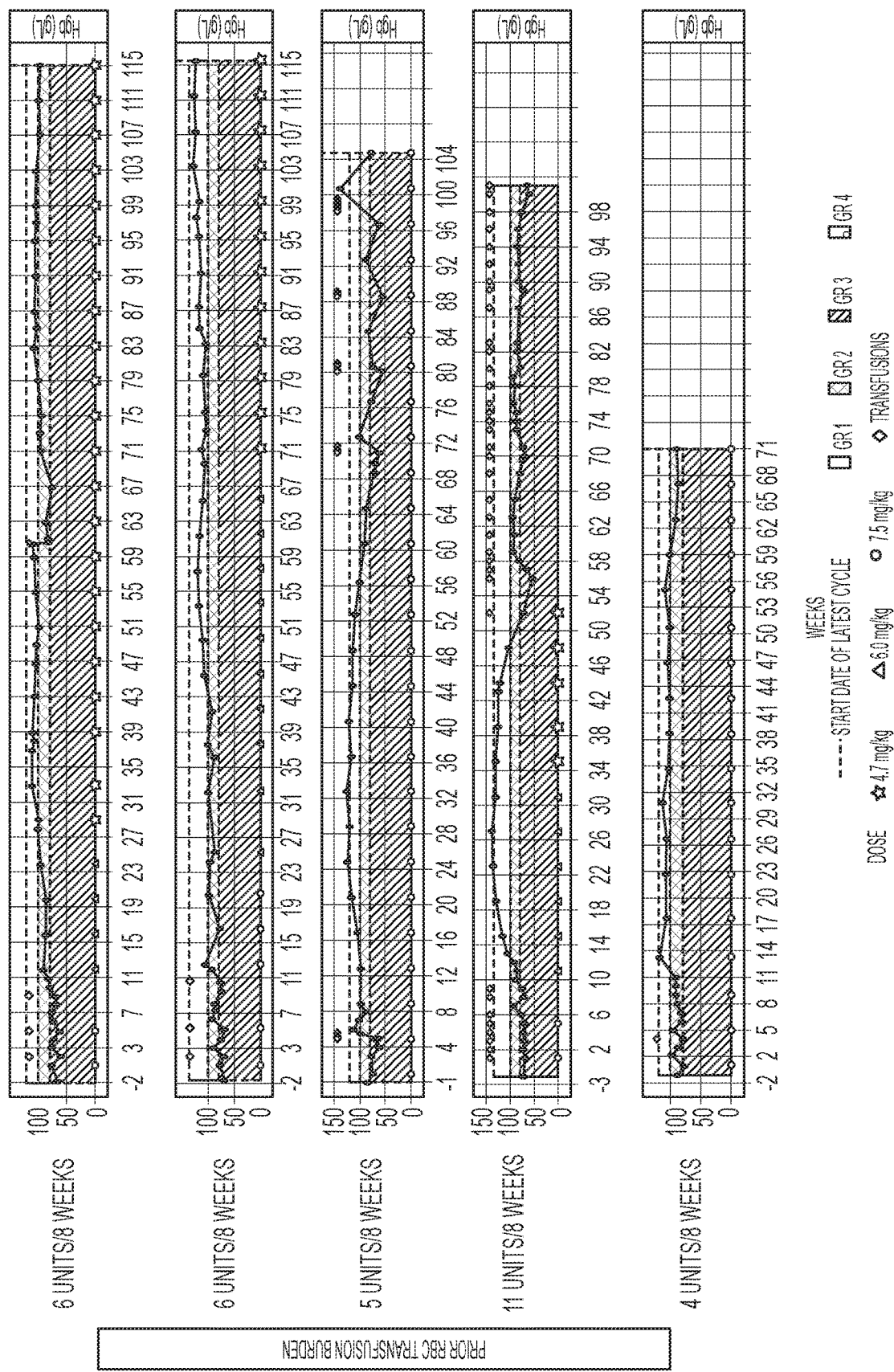
FIG. 6 shows the hemoglobin and imetelstat sodium dosing among patients with durable TI.

FIG. 4 shows the efficacy results in EPO and RS Subgroups at the second data snapshot. Similar efficacy was observed across these subgroups. FIG. 5 shows hematology and imetelstat sodium administration by patients over time at the second data snapshot. FIG. 6 shows the hemoglobin and imetelstat sodium dosing among patients with durable TI. The top three patients in FIG. 6 are still receiving treatment. The top two subjects in FIG. 6 have the longest follow-up.

Safety

Safety findings for those who were lenalidomide/HMA-naive/non-del(5q) were similar to the overall study population.

Table 8 shows the most common treatment emergent adverse events at the second data snapshot. Table 9 shows the occurrence and reversibility of Grade 3/4 Cytopenias. Table 10 shows the maximum post-baseline Common Terminology Criteria for Adverse Events (CTCAE) grade, worsened since baselines for cytopenia by population and safety analysis set at the second data snapshot.

TABLE 8

Most Common Treatment-Emergent Adverse Events (≥10% of Patients in All Treated Patients)

| | All Treated (N = 32) | Lenalidomide and HMA naive and non-del(5q) (n = 13) |
|---|---|---|
| Patients with ≥1 treatment emergent adverse events ("AEs"), n (%) | 31 (97) | 12 (92) |
| Neutropenia | 23 (72) | 7 (54) |
| Thrombocytopenia | 18 (56) | 8 (62) |
| Headache | 8 (25) | 2 (15) |
| Alanine aminotransferase ("ALT") increased | 6 (19) | 3 (23) |
| Aspartate aminotransferase ("AST") increased | 5 (16) | 3 (23) |
| Leukopenia | 5 (16) | 2 (15) |
| Muscle spasms | 5 (16) | 2 (15) |
| Diarrhea | 5 (16) | 2 (15) |
| Anemia | 4 (13) | 2 (15) |
| Asthenia | 4 (13) | 4 (31) |
| Back pain | 4 (13) | 2 (15) |
| Constipation | 4 (13) | 2 (15) |
| Cough | 4 (13) | 1 (8) |
| Dyspnea | 4 (13) | 2 (15) |
| Influenza like illness | 4 (13) | 1 (8) |
| Nausea | 4 (13) | 2 (15) |
| Peripheral edema | 4 (13) | 2 (15) |
| Viral URI | 4 (13) | 4 (31) |

TABLE 9

Occurrence and Reversibility of Grade 3/4 Cytopenias

| | All Treated (N = 32) | Lenalidomide and HMA naive and Non-del(5q) (n = 13) |
|---|---|---|
| Neutrophils, n (%) | | |
| Grade 3 | 8 (25) | 2 (15) |
| Recovered < 4 weeks | 4 (50) | 1 (50) |
| Grade 4 | 13 (41) | 5 (38) |
| Recovered < 4 weeks | 12 (92) | 5 (100) |
| Platelets, n (%) | | |
| Grade 3 | 10 (31) | 5 (38) |
| Recovered <4 weeks | 9 (90) | 5 (100) |
| Grade 4 | 8 (25) | 3 (23) |
| Recovered <4 weeks | 6 (75) | 3 (100) |

Eleven patients received G-CSF during the study for treatment of an adverse event or ongoing medical history (n=10) or as prophylaxis (n=1).

TABLE 10

Maximum Post-baseline CTCAE Grade, Worsened Since Baseline for Cytopenia by Population; Safety Analysis Set

| | All Subjects | Target Population | Other Subjects |
|---|---|---|---|
| Analysis set: safety | 32 | 13 | 19 |
| Neutrophils (×10E9/L) | | | |
| No worsening | 4 (12.5%) | 3 (23.1%) | 1 (5.3%) |
| 1 | 3 (9.4%) | 1 (7.7%) | 2 (10.5%) |
| 2 | 4 (12.5%) | 2 (15.4%) | 2 (10.5%) |
| 3 | 8 (25.0%) | 2 (15.4%) | 6 (31.6%) |
| 4 | 13 (40.6%) | 5 (38.5%) | 8 (42.1%) |
| Platelets (×10E9/L) | | | |
| No worsening | 5 (15.6%) | 2 (15.4%) | 3 (15.8%) |
| 1 | 2 (6.3%) | 1 (7.7%) | 1 (5.3%) |
| 2 | 7 (21.9%) | 2 (15.4%) | 5 (26.3%) |
| 3 | 10 (31.3%) | 5 (38.5%) | 5 (26.3%) |
| 4 | 8 (25.0%) | 3 (23.1%) | 5 (26.3%) |

Note:
Worsened defined as CTCAE grade elevated after baseline. The grade 1-4 summaries categorize subjects according to the maximum grade lab among those labs that have worsened since baseline.
Note the target population includes the subjects who had neither prior HMA nor Len use and no del(5q) at baseline.
Data as per snapshot on May 10, 2018 ("second data snapshot")

Observations (Based on Both Data Snapshots)

The safety and efficacy data for the 32 patients in Part 1 of the study support continued investigation of imetelstat sodium using the current dosing regimen of 7.5 mg/kg every 4 weeks.

At the first data snapshot, 8-week RBC TI was demonstrated in 38% and erythroid HI in 63% of IPSS Low/Int-1 RBC transfusion dependent MDS patients relapsed/refractory to ESA. Durable 24-week TI, with sustained rises in Hb, was observed in 16% of patients.

At the first data snapshot, 54% RBC TI was observed in the 13 patients without del(5q) and without prior exposure to either lenalidomide or HMA (compared to 38% in overall population), and responses were more durable (24-week TI rate of 31%).

Overall, 8-week TI observed in 34% of all patients, with a 24-week TI rate of 16%. The median time to TI was 8.0 weeks. The median duration of TI was 23.1 weeks.

For those patients who were lenalidomide/HMA-naive and non-del(5q), the 8-week and 24-week TI rates were 54% and 31%, respectively. For these patients, the median duration of TI was 42.9 weeks.

Overall, TR (HI-E) was observed in 59% of all patients. The mean relative reduction of RBC transfusion burden from baseline was 60%.

These results support further study of imetelstat sodium (7.5 mg/kg/4 weeks) in IPSS Low/Int-1, TD, ESA-relapsed/refractory MDS. In RBC TD patients with LR-MDS (median: 6 U/8 weeks), imetelstat sodium treatment resulted in erythroid improvement in a majority of patients.

This study was repeated for the target population of 13 subjects with non-del(5q) MDS and without prior exposure to either an HMA or lenalidomide. In this target population, 53.8% achieved the primary endpoint of 8-week RBC TI, compared with 21.1% of other subjects not in the target population. The responses were more durable in the target population than in other subjects (median duration, 42.9 vs 13.9 weeks) and more subjects in the target population achieved 24-week RBC TI (30.8% vs 5.3%). The target population exhibited a comparable or better safety profile for cytopenias and other adverse events, and cytopenias appeared to resolve faster in the target population.

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Numbered Embodiments of the Invention

Exemplary numbered embodiments of the invention are shown below:
1. A method of treating a myelodysplastic syndrome (MDS) comprising administering to a subject in need thereof an effective amount of a telomerase inhibitor, wherein the subject is naive to treatment with an agent selected from a hypomethylating agent (HMA), lenalidomide, and combination thereof.
2. The method of embodiment 1, wherein the MDS is relapsed or refractory MDS.
3. The method of embodiment 1 or embodiment 2, wherein the MDS is MDS relapsed/refractory to erythropoiesis-stimulating agent (ESA).
4. The method of any one of embodiments 1-3, wherein the subject is classified as a low or intermediate-1 IPSS risk MDS subject.
5. The method of any one of embodiments 1-4, wherein the subject is transfusion dependent.
6. The method of embodiment 5, wherein the transfusion dependent subject has a transfusion requirement of about 4 units or more during the 8 weeks prior to the administration of the telomerase inhibitor.
7. The method of any one of embodiments 1-6, wherein the subject is a non-del5q human patient.
8. The method of any one of embodiments 1-7, wherein the subject is classified as a low or intermediate-1 IPSS risk MDS subject and is non-del5q.
9. The method of any one of embodiments 1-8, wherein the subject is naive to treatment with lenalidomide.
10. The method of any one of embodiments 1-9, wherein the HMA is selected from decitabine and azacitidine.
11. The method of embodiment 10, wherein the subject is naive to treatment with decitabine.
12. The method of embodiment 10, wherein the subject is naive to treatment with azacitidine.
13. The method of any one of embodiments 1-12, wherein the telomerase inhibitor is imetelstat.
14. The method of embodiment 13, wherein the imetelstat is imetelstat sodium.
15. The method of embodiment 13, wherein the telomerase inhibitor is imetelstat and is administered for 1, 2, 3, 4, 5, 6, 7, 8 or more than 8 dosage cycles, each cycle comprising:
    (a) intravenous administration of about 7-10 mg/kg imetelstat once every four weeks;
    (b) intravenous administration of about 7-10 mg/kg imetelstat once weekly for four weeks;
    (c) intravenous administration of about 2.5-10 mg/kg imetelstat once every three weeks; or
    (d) intravenous administration of about 0.5-9.4 mg/kg imetelstat once every four weeks.
16. The method of embodiment 15, wherein each dosage cycle comprises intravenous administration of about 7-10 mg/kg imetelstat once every four weeks.
17. The method of embodiment 16, wherein each dosage cycle comprises intravenous administration of about 7.5 mg/kg imetelstat once every four weeks.
18. The method of embodiment 1, wherein the MDS is relapsed or refractory MDS and wherein the subject is classified as a low or intermediate-1 IPSS risk MDS subject.
19. The method of embodiment 18, wherein the subject is transfusion dependent.
20. The method of embodiment 18, wherein the subject is a non-del5q human patient.
21. The method of any one of embodiments 1-20, wherein the subject is naive to treatment with an agent selected from a hypomethylating agent (HMA) and lenalidomide.
22. A telomerase inhibitor for use in treating a myelodysplastic syndrome (MDS) in a subject naive to treatment with an agent selected from a hypomethylating agent (HMA), lenalidomide, and combination thereof.
23. The telomerase inhibitor for use according to embodiment 22, wherein the MDS is relapsed or refractory MDS.
24. The telomerase inhibitor for use according to embodiments 22 or 23, wherein the MDS is MDS relapsed/refractory to erythropoiesis-stimulating agent (ESA).
25. The telomerase inhibitor for use according to any one of embodiments 22-24, wherein the subject is classified as a low or intermediate-1 IPSS risk MDS subject.
26. The telomerase inhibitor for use according to any one of embodiments 22-25, wherein the subject is transfusion dependent.
27. The telomerase inhibitor for use according to embodiment 26, wherein the transfusion dependent subject has a transfusion requirement of about 4 units or more during the 8 weeks prior to the administration of the telomerase inhibitor.
28. The telomerase inhibitor for use according to any one of embodiments 22-27, wherein the subject is a non-del5q human patient.
29. The telomerase inhibitor for use according to embodiment 22, wherein the subject is classified as a low or intermediate-1 IPSS risk MDS subject and is non-del5q.

30. The telomerase inhibitor for use according to any one of embodiments 22-28, wherein the subject is naive to treatment with lenalidomide.
31. The telomerase inhibitor for use according to any one of embodiments 22-29, or 30, wherein the HMA is selected from decitabine and azacitidine.
32. The telomerase inhibitor for use according to embodiment 31, wherein the subject is naive to treatment with decitabine.
33. The telomerase inhibitor for use according to embodiment 31, wherein the subject is naive to treatment with azacitidine.
34. The telomerase inhibitor for use according to any one of embodiments 22-33, wherein the telomerase inhibitor is imetelstat.
35. The telomerase inhibitor for use according to embodiment 34, wherein the imetelstat is imetelstat sodium.
36. The telomerase inhibitor for use according to any one of embodiments 22-35, wherein the MDS is relapsed or refractory MDS and wherein the subject is classified as a low or intermediate-1 IPSS risk MDS subject.
37. The telomerase inhibitor for use according to embodiment 36, wherein the subject is transfusion dependent.
38. The telomerase inhibitor for use according to embodiment 36, wherein the subject is a non-del5q human patient.
39. The telomerase inhibitor for use according any one of embodiments 22-36, wherein the telomerase inhibitor is imetelstat wherein the use comprises administration for 1, 2, 3, 4, 5, 6, 7, 8 or more than 8 dosage cycles, each cycle comprising:
    (a) intravenous administration of about 7-10 mg/kg imetelstat once every four weeks;
    (b) intravenous administration of about 7-10 mg/kg imetelstat once weekly for four weeks;
    (c) intravenous administration of about 2.5-10 mg/kg imetelstat once every three weeks; or
    (d) intravenous administration of about 0.5-9.4 mg/kg imetelstat once every four weeks.
40. The telomerase inhibitor for use according to embodiment 39, wherein each dosage cycle comprises intravenous administration of about 7-10 mg/kg imetelstat once every four weeks.
41. The telomerase inhibitor for use according to embodiment 40, wherein each dosage cycle comprises intravenous administration of about 7.5 mg/kg imetelstat once every four weeks.
42. The telomerase inhibitor for use according to any one of embodiments 22-41, wherein the subject is naive to treatment with an agent selected from a hypomethylating agent (HMA) and lenalidomide.
43. Use of a telomerase inhibitor for treating a myelodysplastic syndrome (MDS) in a subject naive to treatment with an agent selected from a hypomethylating agent (HMA), lenalidomide, and combination thereof.
44. The use according to embodiment 43, wherein the MDS is relapsed or refractory MDS.
45. The use according to embodiments 43 or 44, wherein the MDS is MDS relapsed/refractory to erythropoiesis-stimulating agent (ESA).
46. The use according to any one of embodiments 43-45, wherein the subject is classified as a low or intermediate-1 IPSS risk MDS subject.
47. The use according to any one of embodiments 43-46, wherein the subject is transfusion dependent.
48. The use according embodiment 47, wherein the transfusion dependent subject has a transfusion requirement of about 4 units or more during the 8 weeks prior to the administration of the telomerase inhibitor.
49. The use according to any one of embodiments 43-48, wherein the subject is a non-del5q human patient.
50. The use according to embodiment 43, wherein the subject is classified as a low or intermediate-1 IPSS risk MDS subject and is non-del5q.
51. The use according to any one of embodiments 43-49, wherein the subject is naive to treatment with lenalidomide.
52. The use according to any one of embodiments 43-50, or 51, wherein the HMA is selected from decitabine and azacitidine.
53. The use according to embodiment 52, wherein the subject is naive to treatment with decitabine.
54. The use according to embodiment 52, wherein the subject is naive to treatment with azacitidine.
55. The use according to any one of embodiments 43-54, wherein the telomerase inhibitor is imetelstat.
56. The use according to embodiment 55, wherein the imetelstat is imetelstat sodium.
57. The use according to any one of embodiments 43-56, wherein the MDS is relapsed or refractory MDS and wherein the subject is classified as a low or intermediate-1 IPSS risk MDS subject.
58. The use according to embodiment 57, wherein the subject is transfusion dependent.
59. The use according to embodiment 57, wherein the subject is a non-del5q human patient.
60. The use according any one of embodiments 43-59, wherein the telomerase inhibitor is imetelstat wherein the use comprises administration for 1, 2, 3, 4, 5, 6, 7, 8 or more than 8 dosage cycles, each cycle comprising:
    (a) intravenous administration of about 7-10 mg/kg imetelstat once every four weeks;
    (b) intravenous administration of about 7-10 mg/kg imetelstat once weekly for four weeks;
    (c) intravenous administration of about 2.5-10 mg/kg imetelstat once every three weeks; or
    (d) intravenous administration of about 0.5-9.4 mg/kg imetelstat once every four weeks.
61. The use according to embodiment 60, wherein each dosage cycle comprises intravenous administration of about 7-10 mg/kg imetelstat once every four weeks.
62. The use according to embodiment 61, wherein each dosage cycle comprises intravenous administration of about 7.5 mg/kg imetelstat once every four weeks.
63. The use according to any one of embodiments 43-62, wherein the subject is naive to treatment with an agent selected from a hypomethylating agent (HMA) and lenalidomide.
64. A method of treating a myelodysplastic syndrome (MDS) comprising administering to a subject in need thereof an effective amount of a telomerase inhibitor, wherein the subject is a non-del5q human patient.
65. The method of embodiment 64, wherein the MDS is relapsed or refractory MDS.
66. The method of embodiment 64 or embodiment 65, wherein the MDS is MDS relapsed/refractory to erythropoiesis-stimulating agent (ESA).
67. The method of any one of embodiments 64-66, wherein the subject is classified as a low or intermediate-1 IPSS risk MDS subject.
68. The method of any one of embodiments 64-67, wherein the subject is transfusion dependent.
69. The method of embodiment 68, wherein the transfusion dependent subject has a transfusion requirement of about 4 units or more during the 8 weeks prior to the administration of the telomerase inhibitor.

70. The method of any one of embodiments 64-69, wherein the telomerase inhibitor is imetelstat.

71. The method of embodiment 70, wherein the imetelstat is imetelstat sodium.

72. The method of embodiment 70, wherein the telomerase inhibitor is imetelstat and is administered for 1, 2, 3, 4, 5, 6, 7, 8 or more than 8 dosage cycles, each cycle comprising:
   (a) intravenous administration of about 7-10 mg/kg imetelstat once every four weeks;
   (b) intravenous administration of about 7-10 mg/kg imetelstat once weekly for four weeks;
   (c) intravenous administration of about 2.5-10 mg/kg imetelstat once every three weeks; or
   (d) intravenous administration of about 0.5-9.4 mg/kg imetelstat once every four weeks.

73. The method of embodiment 72, wherein each dosage cycle comprises intravenous administration of about 7-10 mg/kg imetelstat once every four weeks.

74. The method of embodiment 73, wherein each dosage cycle comprises intravenous administration of about 7.5 mg/kg imetelstat once every four weeks.

75. The method of embodiment 64, wherein the MDS is relapsed or refractory MDS and wherein the subject is classified as a low or intermediate-1 IPSS risk MDS subject.

76. The method of embodiment 75, wherein the subject is transfusion dependent.

77. A telomerase inhibitor for use in treating a myelodysplastic syndrome (MDS) in a subject who is a non-del5q human patient.

78. The telomerase inhibitor for use according to embodiment 77, wherein the MDS is relapsed or refractory MDS.

79. The telomerase inhibitor for use according to embodiments 77 or 78, wherein the MDS is MDS relapsed/refractory to erythropoiesis-stimulating agent (ESA).

80. The telomerase inhibitor for use according to any one of embodiments 77-79, wherein the subject is classified as a low or intermediate-1 IPSS risk MDS subject.

81. The telomerase inhibitor for use according to any one of embodiments 77-80, wherein the subject is transfusion dependent.

82. The telomerase inhibitor for use according to embodiment 81, wherein the transfusion dependent subject has a transfusion requirement of about 4 units or more during the 8 weeks prior to the administration of the telomerase inhibitor.

83. The telomerase inhibitor for use according to any one of embodiments 77-82, wherein the telomerase inhibitor is imetelstat.

84. The telomerase inhibitor for use according to embodiment 83, wherein the imetelstat is imetelstat sodium.

85. The telomerase inhibitor for use according to any one of embodiments 77-84, wherein the MDS is relapsed or refractory MDS and wherein the subject is classified as a low or intermediate-1 IPSS risk MDS subject.

86. The telomerase inhibitor for use according to embodiment 85, wherein the subject is transfusion dependent.

87. The telomerase inhibitor for use according any one of embodiments 77-86, wherein the telomerase inhibitor is imetelstat wherein the use comprises administration for 1, 2, 3, 4, 5, 6, 7, 8 or more than 8 dosage cycles, each cycle comprising:
   (a) intravenous administration of about 7-10 mg/kg imetelstat once every four weeks;
   (b) intravenous administration of about 7-10 mg/kg imetelstat once weekly for four weeks;
   (c) intravenous administration of about 2.5-10 mg/kg imetelstat once every three weeks; or
   (d) intravenous administration of about 0.5-9.4 mg/kg imetelstat once every four weeks.

88. The telomerase inhibitor for use according to embodiment 87, wherein each dosage cycle comprises intravenous administration of about 7-10 mg/kg imetelstat once every four weeks.

89. The telomerase inhibitor for use according to embodiment 88, wherein each dosage cycle comprises intravenous administration of about 7.5 mg/kg imetelstat once every four weeks.

90. Use of a telomerase inhibitor for treating a myelodysplastic syndrome (MDS) in a subject who is a non-del5q human patient.

91. The use according to embodiment 90, wherein the MDS is relapsed or refractory MDS.

92. The use according to embodiments 90 or 91, wherein the MDS is MDS relapsed/refractory to erythropoiesis-stimulating agent (ESA).

93. The use according to any one of embodiments 90-92, wherein the subject is classified as a low or intermediate-1 IPSS risk MDS subject.

94. The use according to any one of embodiments 90-93, wherein the subject is transfusion dependent.

95. The use according embodiment 94, wherein the transfusion dependent subject has a transfusion requirement of about 4 units or more during the 8 weeks prior to the administration of the telomerase inhibitor.

96. The use according to any one of embodiments 90-95, wherein the telomerase inhibitor is imetelstat.

97. The use according to embodiment 96, wherein the imetelstat is imetelstat sodium.

98. The use according to any one of embodiments 90-97, wherein the MDS is relapsed or refractory MDS and wherein the subject is classified as a low or intermediate-1 IPSS risk MDS subject.

99. The use according to embodiment 98, wherein the subject is transfusion dependent.

100. The use according any one of embodiments 90-99, wherein the telomerase inhibitor is imetelstat wherein the use comprises administration for 1, 2, 3, 4, 5, 6, 7, 8 or more than 8 dosage cycles, each cycle comprising:
   (a) intravenous administration of about 7-10 mg/kg imetelstat once every four weeks;
   (b) intravenous administration of about 7-10 mg/kg imetelstat once weekly for four weeks;
   (c) intravenous administration of about 2.5-10 mg/kg imetelstat once every three weeks; or
   (d) intravenous administration of about 0.5-9.4 mg/kg imetelstat once every four weeks.

101. The use according to embodiment 100, wherein each dosage cycle comprises intravenous administration of about 7-10 mg/kg imetelstat once every four weeks.

102. The use according to embodiment 101, wherein each dosage cycle comprises intravenous administration of about 7.5 mg/kg imetelstat once every four weeks.

What is claimed is:

1. A method of treating a myelodysplastic syndrome (MDS) in a subject, the method comprising:
classifying the subject as being naïve to treatment with an agent selected from a hypomethylating agent (HMA), lenalidomide, and combination thereof;
selecting the subject for treatment with a telomerase inhibitor because the subject has been classified as being naive to treatment with the agent; and
administering an effective amount of the telomerase inhibitor to the subject to treat the myelodysplastic syndrome.

2. The method of claim 1, wherein the MDS is relapsed or refractory MDS.

3. The method of claim 2, wherein the MDS is MDS relapsed or refractory to an erythropoiesis-stimulating agent (ESA).

4. The method of claim 1, wherein the subject is classified as a low or intermediate-1 IPSS risk MDS subject.

5. The method of claim 1, wherein the subject is transfusion dependent.

6. The method of claim 5, wherein the transfusion dependent subject has a transfusion requirement of about 4 units or more during the 8 weeks prior to the administration of the telomerase inhibitor.

7. The method of claim 1, wherein the subject is a non-del5q human patient.

8. The method of claim 1, wherein the subject is classified as a low or intermediate-1 IPSS risk MDS subject and is non-del5q.

9. The method of claim 1, wherein the subject is naive to treatment with lenalidomide.

10. The method of claim 1, wherein the subject is naive to treatment with a hypomethylating agent (HMA).

11. The method of claim 1, wherein the subject is naive to treatment with lenalidomide and to a hypomethylating agent (HMA).

12. The method of claim 10, wherein the HMA is decitabine.

13. The method of claim 10, wherein the HMA is azacitidine.

14. The method of claim 1, wherein the telomerase inhibitor is imetelstat.

15. The method of claim 14, wherein the imetelstat is imetelstat sodium.

16. The method of claim 14, wherein the telomerase inhibitor is imetelstat and is administered for 1, 2, 3, 4, 5, 6, 7, 8 or more than 8 dosage cycles, each cycle comprising:
(a) intravenous administration of about 7-10 mg/kg imetelstat once every four weeks;
(b) intravenous administration of about 7-10 mg/kg imetelstat once weekly for four weeks;
(c) intravenous administration of about 2.5-10 mg/kg imetelstat once every three weeks; or
(d) intravenous administration of about 0.5-9.4 mg/kg imetelstat once every four weeks.

17. The method of claim 16, wherein each dosage cycle comprises intravenous administration of about 7-10 mg/kg imetelstat once every four weeks.

18. The method of claim 17, wherein each dosage cycle comprises intravenous administration of about 7.5 mg/kg imetelstat once every four weeks.

19. The method of claim 1, wherein the MDS is relapsed or refractory MDS and wherein the subject is classified as a low or intermediate-1 IPSS risk MDS subject.

20. The method of claim 14, wherein the subject is transfusion dependent.

21. The method of claim 14, wherein the subject is a non-del5q human patient.

22. A method of treating a myelodysplastic syndrome (MDS) in a subject, the method comprising:
classifying the subject as being a non-del5q human subject;
selecting the subject for treatment with a telomerase inhibitor because the subject has been classified as being a non-del5q human subject; and
administering an effective amount of the telomerase inhibitor to the subject to treat the myelodysplastic syndrome.

23. The method according to claim 22, wherein the MDS is relapsed or refractory MDS.

24. The method according to claim 23, wherein the MDS is MDS relapsed or refractory to an erythropoiesis-stimulating agent (ESA).

25. The method according to claim 22, wherein the subject is classified as a low or intermediate-1 IPSS risk MDS subject.

26. The method according to claim 22, wherein the subject is transfusion dependent.

27. The method according claim 26, wherein the transfusion dependent subject has a transfusion requirement of about 4 units or more during the 8 weeks prior to the administration of the telomerase inhibitor.

28. The method of claim 23, wherein the subject is naive to treatment with lenalidomide.

29. The method of claim 23, wherein the subject is naive to treatment with a hypomethylating agent (HMA).

30. The method of claim 23, wherein the subject is naive to treatment with lenalidomide and to a hypomethylating agent (HMA).

31. The method of claim 29, wherein the HMA is decitabine.

32. The method of claim 29, wherein the HMA is azacitidine.

33. The method according to claim 23, wherein the telomerase inhibitor is imetelstat.

34. The method according to claim 33, wherein the imetelstat is imetelstat sodium.

35. The method according to claim 33, wherein the MDS is relapsed or refractory MDS and wherein the subject is classified as a low or intermediate-1 IPSS risk MDS subject.

36. The method according to claim 33, wherein the subject is transfusion dependent.

37. The method according to claim 33, wherein the telomerase inhibitor is imetelstat wherein the use comprises administration for 1, 2, 3, 4, 5, 6, 7, 8 or more than 8 dosage cycles, each cycle comprising:
   (a) intravenous administration of about 7-10 mg/kg imetelstat once every four weeks;
   (b) intravenous administration of about 7-10 mg/kg imetelstat once weekly for four weeks;
   (c) intravenous administration of about 2.5-10 mg/kg imetelstat once every three weeks; or
   (d) intravenous administration of about 0.5-9.4 mg/kg imetelstat once every four weeks.

38. The method according to claim 37, wherein each dosage cycle comprises intravenous administration of about 7-10 mg/kg imetelstat once every four weeks.

39. The method according to claim 38, wherein each dosage cycle comprises intravenous administration of about 7.5 mg/kg imetelstat once every four weeks.

* * * * *